United States Patent
Hawes et al.

(10) Patent No.: US 11,071,326 B2
(45) Date of Patent: Jul. 27, 2021

(54) E-VAPING DEVICE

(71) Applicant: Altria Client Services LLC, Richmond, VA (US)

(72) Inventors: Eric Hawes, Glen Allen, VA (US); Raymond W. Lau, Richmond, VA (US); Mik Dahl, Lapu-Lapu (PH); Jon Jarantilla, Lapu-Lapu (PH); Galen Salvador, Lapu-Lapu (PH); Jose Jesus Paolo Montalvan, Mandaue (PH); Jeroen Kok, Amsterdam (NL)

(73) Assignee: Altria Client Services LLC, Richmond, VA (US)

( * ) Notice: Subject to any disclaimer, the term of this patent is extended or adjusted under 35 U.S.C. 154(b) by 199 days.

(21) Appl. No.: 16/196,219

(22) Filed: Nov. 20, 2018

(65) Prior Publication Data

US 2020/0154781 A1 May 21, 2020

(51) Int. Cl.
*A24F 40/485* (2020.01)

(52) U.S. Cl.
CPC ................... *A24F 40/485* (2020.01)

(58) Field of Classification Search
CPC ............... A24F 40/42; A24F 40/485
See application file for complete search history.

(56) References Cited

U.S. PATENT DOCUMENTS

| 9,247,773 | B2 | 2/2016 | Memari et al. |
| 9,254,007 | B2 | 2/2016 | Liu |
| 9,308,336 | B2 | 4/2016 | Newton |

(Continued)

FOREIGN PATENT DOCUMENTS

| CN | 203538369 | 4/2014 |
| CN | 203748684 U | 8/2014 |

(Continued)

OTHER PUBLICATIONS

Anonymous: "iJust 2 Airflow Control Ring." Retrieved from the Internet on Nov. 16, 2018. URL: https://www.eleafus.com/ijust-2-airflow-control-ring.html.

(Continued)

*Primary Examiner* — Michael H. Wilson
*Assistant Examiner* — Stephanie Lynn Moore
(74) *Attorney, Agent, or Firm* — Harness, Dickey & Pierce, P.L.C.

(57) ABSTRACT

In some example embodiments, a reservoir assembly may include a reservoir and an isolation structure. The reservoir may hold a pre-vapor formulation. The reservoir may include a first fluid port extending through a housing of the reservoir, where the first fluid port may enable fluid communication between the reservoir and an exterior of the reservoir assembly. The reservoir may be coupled to a vaporizer assembly that includes a second fluid port configured to enable fluid communication between the reservoir and vaporizer assembly, or the reservoir may be coupled to a vaporizer connector assembly that includes a second fluid port configured to enable fluid communication between the reservoir and an exterior through the vaporizer connector assembly. The isolation structure may move in relation to the reservoir and the vaporizer connector assembly to a position where it exposes one of the fluid ports and covers the other.

18 Claims, 12 Drawing Sheets

(56) References Cited

U.S. PATENT DOCUMENTS

| | | |
|---|---|---|
| 9,750,282 B2 | 9/2017 | Liu |
| 9,795,169 B1 | 10/2017 | Zhu |
| 9,814,264 B2 | 11/2017 | Coelho Belo Fernandes De Carvalho |
| 9,907,341 B1 | 3/2018 | Zhu |
| 9,961,942 B2 | 5/2018 | Liu |
| 9,993,025 B2 | 6/2018 | Alarcon et al. |
| 2014/0290674 A1 | 10/2014 | Liu |
| 2015/0128971 A1 | 5/2015 | Verleur et al. |
| 2015/0196055 A1 | 7/2015 | Liu |
| 2015/0335071 A1* | 11/2015 | Brinkley ............ H05B 1/0297 131/328 |
| 2016/0007654 A1 | 1/2016 | Zhu |
| 2016/0073692 A1 | 3/2016 | Alarcon et al. |
| 2016/0095357 A1 | 4/2016 | Burton |
| 2016/0120226 A1 | 5/2016 | Rado |
| 2016/0120227 A1 | 5/2016 | Levitz et al. |
| 2016/0157522 A1 | 6/2016 | Zhu |
| 2016/0219938 A1 | 8/2016 | Mamoun et al. |
| 2016/0262452 A1 | 9/2016 | Zhu |
| 2016/0286860 A1 | 10/2016 | Flayler |
| 2017/0001854 A1 | 1/2017 | Li et al. |
| 2017/0013880 A1 | 1/2017 | O'Brien et al. |
| 2017/0027227 A1 | 2/2017 | Lipowicz |
| 2017/0065001 A1 | 3/2017 | Li et al. |
| 2017/0071251 A1 | 3/2017 | Goch |
| 2017/0105451 A1 | 4/2017 | Fornarelli |
| 2017/0113007 A1 | 4/2017 | Wu |
| 2017/0156408 A1 | 6/2017 | Li et al. |
| 2017/0188636 A1 | 7/2017 | Li et al. |
| 2017/0208869 A1 | 7/2017 | Li et al. |
| 2017/0238614 A1 | 8/2017 | Li et al. |
| 2017/0280778 A1 | 10/2017 | Force |
| 2017/0290370 A1 | 10/2017 | Garthaffner et al. |
| 2017/0354180 A1 | 12/2017 | Fornarelli |
| 2018/0007961 A1 | 1/2018 | Zhu |
| 2018/0007966 A1 | 1/2018 | Li et al. |
| 2018/0020726 A1 | 1/2018 | Alarcon et al. |
| 2018/0035718 A1 | 2/2018 | Liu |
| 2018/0077967 A1 | 3/2018 | Hatton et al. |
| 2018/0077968 A1 | 3/2018 | Qiu |
| 2018/0098573 A1 | 4/2018 | Yu et al. |
| 2018/0098575 A1 | 4/2018 | Liu |
| 2018/0110940 A1 | 4/2018 | Suzuki et al. |
| 2018/0168236 A1 | 6/2018 | Qiu |
| 2018/0199631 A1* | 7/2018 | Chen ............... A61M 15/06 |
| 2018/0279691 A1 | 10/2018 | Li et al. |
| 2018/0280636 A1 | 10/2018 | Jiang et al. |

FOREIGN PATENT DOCUMENTS

| | | | |
|---|---|---|---|
| CN | 104082863 A | 10/2014 | |
| CN | 203851819 | 10/2014 | |
| CN | 203860454 | 10/2014 | |
| CN | 203860455 | 10/2014 | |
| CN | 203986123 | 12/2014 | |
| CN | 204048044 U | 12/2014 | |
| CN | 204104840 U | 1/2015 | |
| CN | 104544568 A | 4/2015 | |
| CN | 204801175 U | 12/2015 | |
| CN | 105310112 A | 2/2016 | |
| CN | 205390305 U | 7/2016 | |
| CN | 105815810 A | 8/2016 | |
| CN | 105942581 A | 9/2016 | |
| CN | 205695706 | 11/2016 | |
| CN | 205865989 | 1/2017 | |
| CN | 106418714 A | 2/2017 | |
| CN | 107095346 A | 8/2017 | |
| CN | 206380711 | 8/2017 | |
| CN | 206413751 | 8/2017 | |
| CN | 206453250 | 9/2017 | |
| CN | 206534130 | 10/2017 | |
| CN | 107373758 A | 11/2017 | |
| CN | 107411173 A | 12/2017 | |
| CN | 107411176 A | 12/2017 | |
| CN | 206866629 | 1/2018 | |
| CN | 206978739 | 2/2018 | |
| CN | 206978745 | 2/2018 | |
| CN | 207040881 | 2/2018 | |
| CN | 207100510 | 3/2018 | |
| CN | 207167762 | 4/2018 | |
| CN | 207185918 | 4/2018 | |
| CN | 207252783 | 4/2018 | |
| CN | 107981418 A | 5/2018 | |
| CN | 207306063 | 5/2018 | |
| CN | 207306075 | 5/2018 | |
| CN | 207306079 | 5/2018 | |
| DE | 202014001717 U1 | 5/2015 | |
| EP | 2856892 A1 | 4/2015 | |
| EP | 3031339 A1 * | 6/2016 | ........... A24F 47/008 |
| EP | 3254571 A1 | 12/2017 | |
| EP | 3275322 A1 | 1/2018 | |
| EP | 3305110 A2 | 4/2018 | |
| EP | 3338571 A2 | 6/2018 | |
| WO | WO-2014/187770 A2 | 11/2014 | |
| WO | WO-2014201432 A1 | 12/2014 | |
| WO | WO-2015/062136 A1 | 5/2015 | |
| WO | WO-2015/117704 A1 | 8/2015 | |
| WO | WO-2016/008217 A1 | 1/2016 | |
| WO | WO-2016045058 A1 | 3/2016 | |
| WO | WO-2016/096780 A1 | 6/2016 | |
| WO | WO-2016090426 A1 | 6/2016 | |
| WO | WO-2016119098 A1 | 8/2016 | |
| WO | WO-2016141508 A1 | 9/2016 | |
| WO | WO-2016145612 A1 | 9/2016 | |
| WO | WO-2016145613 A1 | 9/2016 | |
| WO | WO-2016/154994 A1 | 10/2016 | |
| WO | WO-2016/155103 A1 | 10/2016 | |
| WO | WO-2016201602 A1 | 12/2016 | |
| WO | WO-2017033132 A1 | 3/2017 | |
| WO | WO-2017063535 A1 | 4/2017 | |
| WO | WO-2017113513 A1 | 7/2017 | |
| WO | WO-2017118135 A1 | 7/2017 | |
| WO | WO-2017124334 A1 | 7/2017 | |
| WO | WO-2017156733 A1 | 9/2017 | |
| WO | WO-2017190602 A1 | 11/2017 | |

OTHER PUBLICATIONS

Anonymous: "Newest Hurricane RTA Atomizer Adjustable Airflow E-Phoenix Hurricane RBA Tank VS Fire Bird Goblin Mini Kayfun V3 Mini Vaporizers DHL." Retrieved from the Internet Nov. 16, 2018. URL: https://www.dhgate.com/product/newest-hurricane-rta-atomizer-adjustable/377737091.html.

Anonymous: "China eCig Supplier Elego Wholesale Huge Vapor Starter Kit 2200mah Yocan X-linx." Retrieved from the Internet Nov. 16, 2018. URL: https://www.alibaba.com/product-detail/China-eCig-Supplier-Elego-Wholesale-Huge_60332730872.html?spm=a2700.7724857.normalList.5.785a140b%E2%80%A6.

Anonymous: "ShenRay TAE Adjustable Airflow Atomizer 5ml Capacity Vaporizer 25mm RTA Electronic Cigarette rta Vape." Retrieved from the Internet Nov. 16, 2018. URL: https://www.aliexpress.com/item/ShenRay-TAE-Adjustable-Airflow-Atomizer-5ml-Capacity-Vaporizer-25mm-RTA-Electronic-Cigarette-rta-Vape/328461%E2%80%A6.

Anonymous: "OBS T-VCT Sub Ohm Tank E-Cigarette 6ml RBA Atomizer with 0.25o." Retrieved from the internet Nov. 16, 2018. URL: https://www.gearbest.com/electronic-cigarettes/pp_187373.html.

Anonymous: "SER Little 16mm RDA Atomizer—SILVER." Retrieved from the internet Nov. 16, 2018. URL: https://www.gearbest.com/vapor-styles/pp_618116.html.

Anonymous: "Authentic Aspire Mini Nautilus E-Cigarette Atomizer Kit—SILVER." Retrieved from the Internet Nov. 16, 2018. URL: https://www.gearbest.com/electronic-cigarettes/pp_104356.html.

International Search Report and Written Opinion thereof dated Feb. 24, 2020 for corresponding International Application No. PCT/EP2019/081972.

(56) References Cited

OTHER PUBLICATIONS

International Search Report and Written Opinion thereof dated Feb. 19, 2020 for corresponding International Application No. PCT/EP2019/081987.
International Search Report and Written Opinion thereof dated Feb. 19, 2020 for corresponding International Application No. PCT/EP2019/081985.
International Search Report and Written Opinion thereof dated Feb. 14, 2020 for corresponding International Application No. PCT/EP2019/081970.
Written Opinion dated Nov. 3, 2020 for corresponding International Application No. PCT/EP2019/081970.
International Preliminary Report on Patentability dated Mar. 5, 2021 for corresponding International Application No. PCT/EP2019/081970.
Written Opinion dated Oct. 22, 2020 for corresponding International Application No. PCT/EP2019/081985.
U.S. Office Action dated Oct. 28, 2020 for corresponding U.S. Appl. No. 16/196,344.
International Preliminary Report on Patentability dated Feb. 16, 2021 for corresponding International Application No. PCT/EP2019/081985.
U.S. Office Action dated Nov. 23, 2020 for corresponding U.S. Appl. No. 16/196,749.
U.S. Office Action dated Mar. 31, 2021 for corresponding U.S. Appl. No. 16/196,344.
U.S. Notice of Allowance dated Apr. 14, 2021 for corresponding U.S. Appl. No. 16/196,749.
U.S. Office Action dated May 10, 2021 for U.S. Appl. No. 16/196,866.
International Preliminary Report on Patentability dated May 25, 2021 for corresponding International Application No. PCT/EP2019/081987.

* cited by examiner

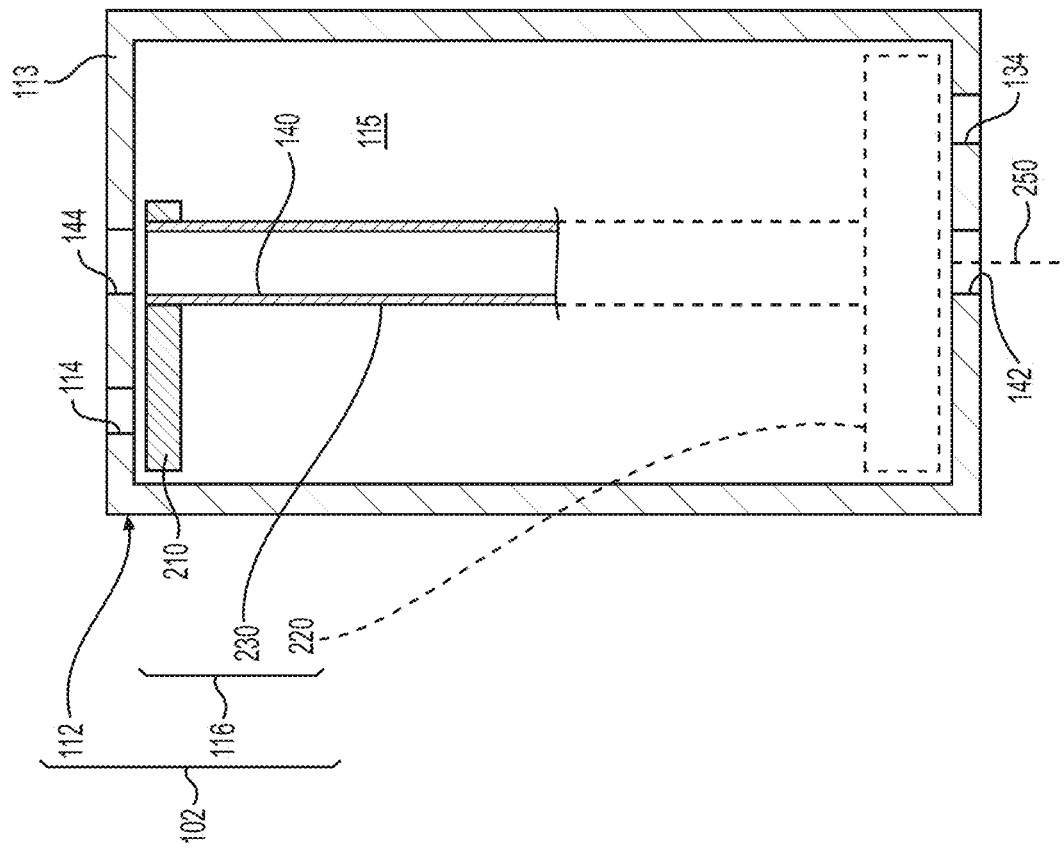
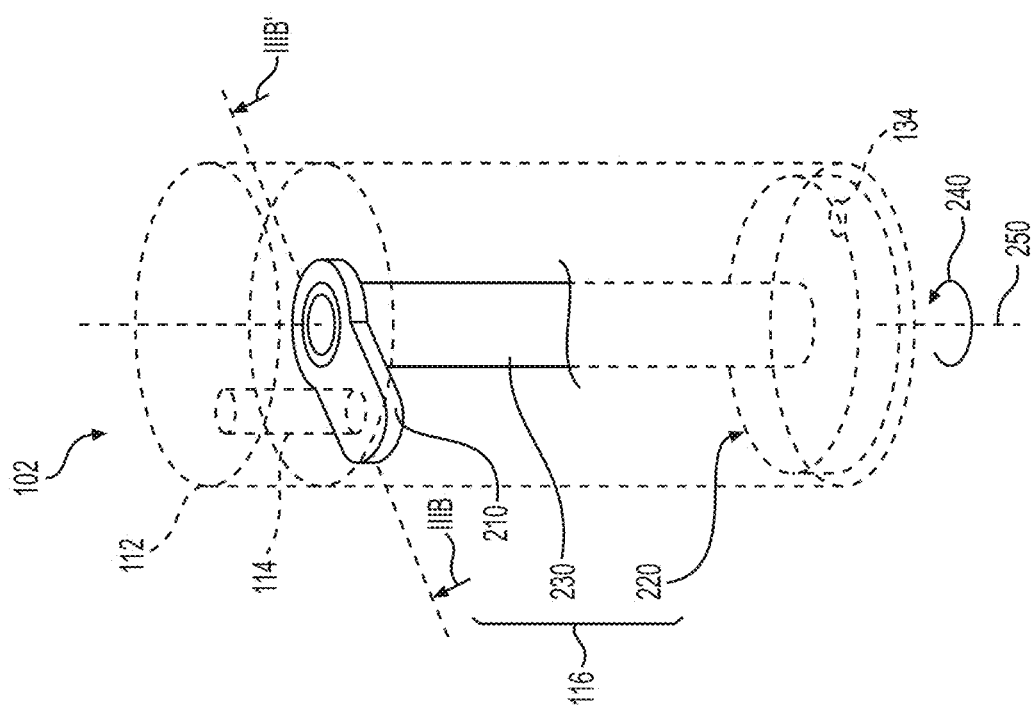
FIG. 3A
FIG. 3B

E-VAPING DEVICE

BACKGROUND

Field

Example embodiments relate to electronic vaping devices, e-vaping devices, or the like.

Description of Related Art

E-vaping devices, also referred to herein as electronic vaping devices (EVDs) may be used by adult vapers for fluid portable vaping. An e-vaping device may include a reservoir that holds pre-vapor formulation and a vaporizer assembly that may heat pre-vapor formulation drawn from the reservoir to generate a vapor.

Some e-vaping devices are configured to enable replenishment of the pre-vapor formulation held in a reservoir of the e-vaping device (i.e., refilling of the reservoir).

SUMMARY

In some example embodiments, a vapor generator assembly may include a reservoir, a vaporizer assembly, and an isolation structure. The reservoir may be configured to hold a pre-vapor formulation. The reservoir may include a first fluid port extending through a housing of the reservoir. The first fluid port may be configured to enable fluid communication between the reservoir and an exterior of the vapor generator assembly. The vaporizer assembly may be configured to vaporize the pre-vapor formulation. The vaporizer assembly may include a second fluid port extending through a housing of the vaporizer assembly. The second fluid port may be configured to enable fluid communication between the reservoir and the vaporizer assembly. The isolation structure may be configured to move in relation to both the reservoir and the vaporizer assembly to a position where the isolation structure exposes the first fluid port and covers the second fluid port.

The isolation structure may be configured to move in relation to both the reservoir and the vaporizer assembly to a second position where the isolation structure exposes the second fluid port and covers the first fluid port.

The isolation structure may be configured to move in relation to both the reservoir and the vaporizer assembly to a third position where the isolation structure covers the first fluid port and covers the second fluid port.

The reservoir may be configured to be refilled through the first fluid port when the isolation structure is in the position where the isolation structure exposes the first fluid port and covers the second fluid port.

The housing of the vaporizer assembly and the housing of the reservoir may form at least a portion of a common housing.

The isolation structure may include a first structure. The first structure may include a third fluid port extending through the first structure. The third fluid port may be configured to at least partially align with the first fluid port for the isolation structure to expose the first fluid port.

The isolation structure may include a second structure. The second structure may include a fourth fluid port extending through the second structure. The fourth fluid port may be configured to at least partially align with the second fluid port for the isolation structure to expose the second fluid port.

The second structure may include a cylindrical structure, and the fourth fluid port may extend through the cylindrical structure.

The isolation structure may include a third fluid port extending through the isolation structure. The third fluid port may be configured to at least partially align with the second fluid port for the isolation structure to expose the second fluid port.

The vapor generator assembly may include a vaporizer connector assembly configured to detachably couple the vaporizer assembly and the reservoir. The vaporizer connector assembly may include a third fluid port extending through the vaporizer connector assembly. The third fluid port may be configured to align with the second fluid port. The isolation structure may expose the second fluid port and the third fluid port in the second position.

According to some example embodiments, an e-vaping device may include the vapor generator assembly and a power supply assembly coupled to the vapor generator assembly. The power supply assembly may include a power supply. The power supply assembly may be configured to supply electrical power from the power supply to the vaporizer assembly.

The power supply may be a rechargeable battery.

The power supply assembly may be configured to decouple from the vapor generator assembly.

According to some example embodiments, a reservoir assembly for an e-vaping device may include a reservoir, a vaporizer connector assembly, and an isolation structure. The reservoir may be configured to hold a pre-vapor formulation. The reservoir may include a first fluid port extending through a housing of the reservoir. The first fluid port may be configured to enable fluid communication between the reservoir and an exterior of the reservoir assembly. The vaporizer connector assembly may be configured to couple with a vaporizer assembly. The vaporizer connector assembly may include a second fluid port extending through the vaporizer connector assembly. The second fluid port may be configured to enable fluid communication between the reservoir and the exterior of the reservoir assembly through the vaporizer connector assembly. The isolation structure may be configured to move in relation to both the reservoir and the vaporizer connector assembly to a position where the isolation structure exposes the first fluid port and covers the second fluid port.

The isolation structure may be configured to move in relation to both the reservoir and the vaporizer connector assembly to a second position where the isolation structure exposes the second fluid port and covers the first fluid port.

The isolation structure may be configured to move in relation to both the reservoir and the vaporizer connector assembly to a third position where the isolation structure covers the first fluid port and covers the second fluid port.

The isolation structure may include a first structure. The first structure may include a third fluid port extending through the first structure. The third fluid port may be configured to at least partially align with the first fluid port for the isolation structure to expose the first fluid port.

The isolation structure may include a second structure. The second structure may include a fourth fluid port extending through the second structure. The fourth fluid port may be configured to at least partially align with the second fluid port for the isolation structure to expose the second fluid port.

The second structure may include a cylindrical structure. The fourth fluid port may extend through the cylindrical structure.

The isolation structure may include a third fluid port extending through the isolation structure. The third fluid port may be configured to at least partially align with the second fluid port for the isolation structure to expose the second fluid port.

The second structure may include a cylindrical structure. The second structure may include a fourth fluid port extending through the second structure. The fourth fluid port may be configured to at least partially align with the second fluid port for the isolation structure to expose the second fluid port.

The vaporizer connector assembly may be configured to detachably couple with the vaporizer assembly.

According to some example embodiments, a vapor generator assembly may include a reservoir, a vaporizer assembly, and an isolation structure. The reservoir may be configured to hold a pre-vapor formulation. The reservoir may include a first fluid port configured to enable fluid communication between the reservoir and an exterior of the reservoir. The vaporizer assembly may include a second fluid port configured to enable fluid communication between the reservoir and the vaporizer assembly. The isolation structure may be configured to move in relation to both the reservoir and the vaporizer assembly to a position where the isolation structure enables fluid communication through the first fluid port and disables fluid communication through the second fluid port.

The isolation structure may be configured to move in relation to both the reservoir and the vaporizer assembly to a second position where the isolation structure enables fluid communication through the second fluid port and disables fluid communication through the first fluid port.

The isolation structure may be configured to move in relation to both the reservoir and the vaporizer assembly to a third position where the isolation structure disables fluid communication through the second fluid port and disables fluid communication through the first fluid port.

BRIEF DESCRIPTION OF THE DRAWINGS

The various features and advantages of the non-limiting example embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 3A is a perspective of a reservoir assembly according to some example embodiments.

FIG. 3B is a cross-sectional view along line IIIB-IIIB' of the reservoir assembly of FIG. 3A according to some example embodiments.

DETAILED DESCRIPTION OF EXAMPLE EMBODIMENTS

Figure 1A:
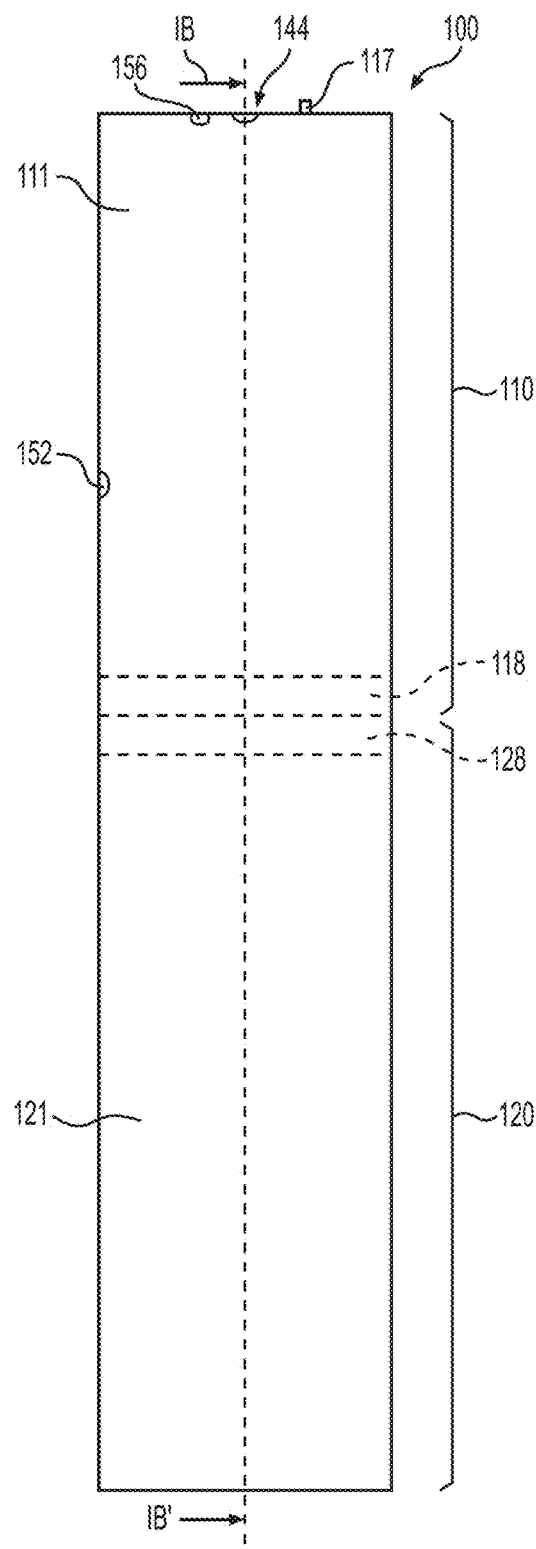
FIG. 1A is a side view of an e-vaping device according to some example embodiments.

Some detailed example embodiments are disclosed herein. However, specific structural and functional details disclosed herein are merely provided for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element, or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, etc., but do not preclude the presence or addition of one or more other features, integers, steps, operations, elements, etc., and/or groups thereof.

When the words "about" and "substantially" are used in this specification in connection with a numerical value, it is intended that the associated numerical value include a tolerance of ±10% around the stated numerical value, unless otherwise explicitly defined.

Example embodiments are described herein with reference to cross-sectional illustrations that are schematic illustrations of example embodiments. As such, variations from the shapes of the illustrations are to be expected. Thus, example embodiments should not be construed as limited to the shapes of regions illustrated herein but are to include deviations in shapes.

Vapor, aerosol and dispersion are used interchangeably and are meant to cover the matter generated or outputted by the devices disclosed, claimed and/or equivalents thereof.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Figure 1B:
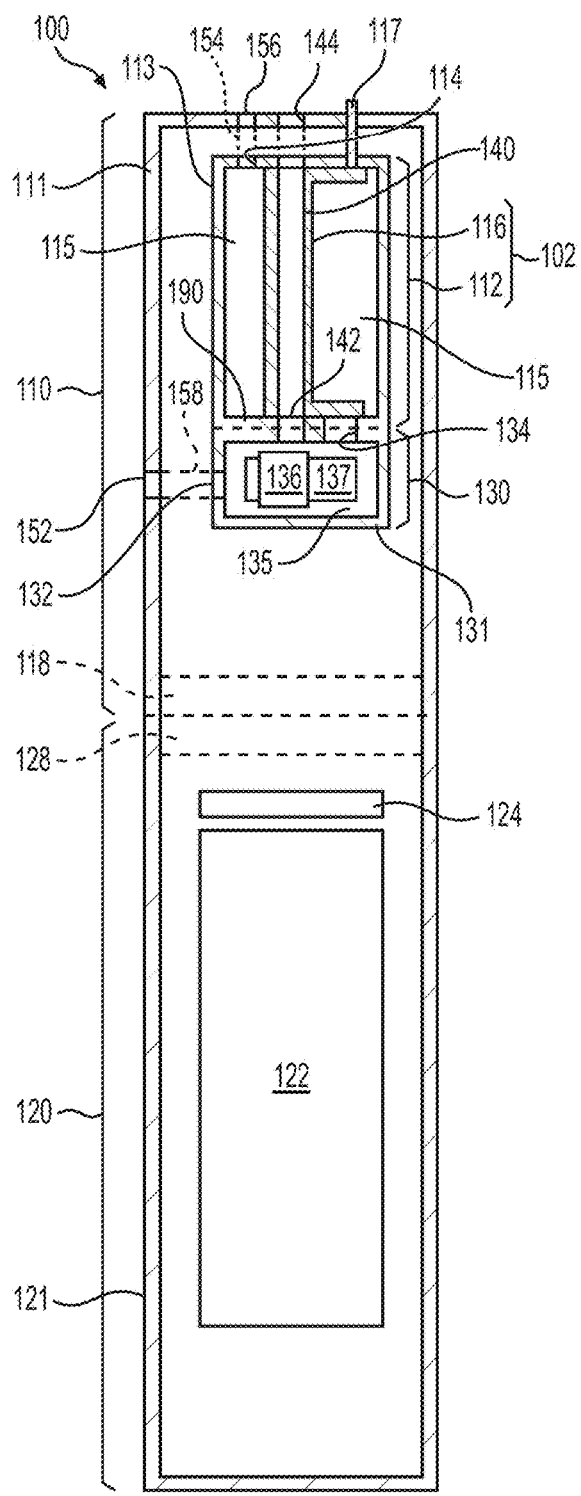
FIG. 1B is a cross-sectional view along line IB-IB' of the e-vaping device of FIG. 1A according to some example embodiments.

FIG. 1A is a side view of an e-vaping device 100 according to some example embodiments. FIG. 1B is a cross-sectional view along line IB-IB' of the e-vaping device 100 of FIG. 1A according to some example embodiments. As used herein, the term "e-vaping device" is inclusive of all types of electronic vaping devices, regardless of form, size or shape.

Referring to FIGS. 1A-1B, the e-vaping device 100 includes a vapor generator assembly 110 and a power supply assembly 120. In some example embodiments, the vapor generator assembly 110 and power supply assembly 120 include respective complementary connector assemblies 118, 128 and are configured to be detachably connected to each other based on detachably coupling the connector assemblies 118, 128 together. In some example embodiments, a vapor generator assembly 110 that is configured to be detachably coupled to a power supply assembly 120 to form an e-vaping device 100 may be referred to herein as a cartridge. In some example embodiments, the connector assemblies 118, 128 include threaded connectors. It should be appreciated that a connector assembly 118, 128 may be any type of connector, including, without limitation, a snug-fit, detent, clamp, bayonet, sliding fit, sleeve fit, alignment fit, threaded connector, magnetic, clasp, or any other type of connection, and/or combinations thereof. In some example embodiments, the e-vaping device 100 may be a unitary piece that includes the vapor generator assembly 110 and the power supply assembly 120 in the unitary piece, instead of including the vapor generator assembly 110 and the power supply assembly 120 as separate pieces that are coupled together to form the e-vaping device 100.

As shown in FIGS. 1A-1B, the vapor generator assembly 110 may include a reservoir 112, a vaporizer assembly 130, and an isolation structure 116. As shown in FIGS. 1A-1B, the reservoir 112 and the isolation structure 116 may be included in a reservoir assembly 102 of some example embodiments.

As shown in FIGS. 1A-1B, the vapor generator assembly 110 may include an outer housing 111. In the example embodiments shown in at least FIG. 1B, the reservoir 112 and the vaporizer assembly 130 may be located within an interior space defined by the outer housing 111, such that the outer housing 113 of the reservoir 112 and the outer housing 131 of the vaporizer assembly 130 are separate from the outer housing 111 of the vapor generator assembly 110. But, it will be understood that, in some example embodiments, the outer housing 111 of the vapor generator assembly 110 may comprise the outer housing 113 of the reservoir 112 and/or the outer housing 131 of the vaporizer assembly 130. In some example embodiments, including the example embodiments shown in FIG. 1B, the outer housing 113 of the reservoir 112 and the outer housing 131 of the vaporizer assembly form part of a unitary piece of material; in other words, in some example embodiments, housings 113 and 131 are separate connectable housings, and in some example embodiments housings 113 and 131 form at least a portion of a common housing.

The reservoir 112 may include an outer housing 113 that at least partially defines an interior space 115. The reservoir 112 may be configured to hold a pre-vapor formulation within the interior of the reservoir 112, where the interior may include the interior space 115 at least partially defined by the outer housing 113 of the reservoir 112.

As shown in at least FIG. 1B, the reservoir 112 may include a fluid port 114, which extends through the outer housing 113 of the reservoir 112 between the interior space 115 of the reservoir 112 and an exterior of at least the reservoir 112, such that the fluid port 114 may enable fluid communication between the reservoir 112 and the exterior of at least the reservoir 112.

As shown in at least FIGS. 1A-1B, in some example embodiments, the fluid port 114 may be coupled to a conduit 154 that extends from fluid port 114 to a fluid port 156 that is directly exposed to the exterior of the vapor generator assembly 110 (e.g., an ambient environment), such that the fluid port 114 is configured to enable fluid communication between the reservoir 112 and the exterior of the vapor generator assembly 110 via conduit 154 and fluid port 156. In some example embodiments, for example where the outer housing 113 of the reservoir 112 defines at least a portion of the outer housing 111 of the vapor generator assembly 110, the fluid port 114 may be directly exposed to the exterior of the vapor generator assembly 110 (e.g., the ambient environment), such that conduit 154 and fluid port 156 may be omitted from the vapor generator assembly 110.

As shown in at least FIG. 1B, the vaporizer assembly 130 may include an outer housing 131 that at least partially defines an interior space 135 of the vaporizer assembly 130. As further shown in at least FIG. 1B, the vaporizer assembly 130 may include a fluid port 134, which extends through the outer housing 131 of the vaporizer assembly 130 between the interior space 135 of the vaporizer assembly 130 and an exterior of the vaporizer assembly 130, such that the fluid port 134 may enable fluid communication between elements at least partially located within the interior space 135 and an exterior of the vaporizer assembly 130. As further shown in FIG. 1B, the fluid port 134 may enable fluid communication between the reservoir 112 and the vaporizer assembly 130. In some example embodiments, the fluid port 134 extends through the outer housing 113 of the reservoir 112, in addition to or instead of extending through the outer housing 131 of the vaporizer assembly 130. In some example embodiments, the outer housing 113 and the outer housing 131 are part of the same housing, and fluid port 134 extends through said housing.

As shown in FIG. 1B, the housing 190 separating the reservoir 112 from the vaporizer assembly 130 may form part of the outer housing 113 of the reservoir 112, may form part of the outer housing 131 of the vaporizer assembly 130, may include a housing that is separate from the outer housings 113, 131, a sub-combination thereof, or a combination thereof. As described further below, the reservoir assembly 102 may include a vaporizer connector assembly that is configured to detachably couple the vaporizer assembly 130 with the reservoir 112, and the vaporizer connector assembly may at least partially define an interior space 115 of the reservoir 112.

The vaporizer assembly 130 may include a heater 136 and a dispensing interface 137. The dispensing interface 137 may be in fluid communication with the fluid port 134, such that the dispensing interface 137 is configured to be in fluid communication with the reservoir 112 through at least the fluid port 134, such that pre-vapor formulation drawn into the interior space 135 through fluid port 134 may be drawn by the dispensing interface 137 to be in fluid communication with the heater 136. The heater 136 (also referred to herein as a heating element) may heat pre-vapor formulation drawn from the reservoir 112 through the fluid port 134 (e.g., at least partially by the dispensing interface 137 or independently of any dispensing interface) to generate a vapor.

As further shown in FIG. 1B, the vapor generator assembly 110 may include an inlet port 152, extending through the outer housing 111 of the vapor generator assembly 110, and a conduit 158, coupling inlet ports 152, 132, that are configured to direct air from an exterior of the vapor generator assembly 110 (e.g., an ambient environment) to flow into the vaporizer assembly 130, via at least inlet port 132 in the outer housing 131 of the vaporizer assembly 130, to flow in fluid communication with the heater 136. In some example embodiments, wherein the outer housing 111 of the vapor generator assembly 110 includes the outer housing 131 of the vaporizer assembly 130, the inlet port 152 and conduit 158 may be omitted from the vapor generator assembly 110 and the inlet port 132 may be directly exposed to the exterior of the vapor generator assembly 110 (e.g., an ambient environment).

As further shown in FIGS. 1A-1B, the vaporizer assembly 130 may include an outlet port 142 extending through the outer housing 131 of the vaporizer assembly 130, the vapor generator assembly 110 may include an outlet port 144 extending through an outer housing 111 of the vapor generator assembly, and the vapor generator assembly 110 may further include a conduit 140 coupling the outlet ports 142, 144 to establish fluid communication between the vaporizer assembly 130 and the exterior of the vapor generator assembly 110 (e.g., the ambient environment).

In operation of an e-vaping device 100 according to some example embodiments, air may be drawn into the vaporizer assembly 130 through at least the inlet port 132, vapor generated by the heater 136 may be entrained in the air that is drawn into the vaporizer assembly 130, and a mixture of the air and entrained vapor may be drawn from the vaporizer assembly 130 to the exterior of the vapor generator assembly 110 through outlet port 142, conduit 140, and outlet port 144. As shown in FIG. 1B, the outlet port 142 may extend through the outer housing 131 of the vaporizer assembly 130, the outer housing 113 of the reservoir 112, a vaporizer connector assembly, a housing 190, a sub-combination thereof, or a combination thereof.

In some example embodiments, reservoir assembly 102 is configured to enable refilling of the pre-vapor formulation held in reservoir 112. As shown in FIG. 1B, the fluid port 114 may enable fluid communication between the reservoir 112 and an exterior of at least the reservoir 112, which in some examples may be independently of the vaporizer assembly 130 and/or conduit 140. Thus, the reservoir assembly 102 may be configured to enable refilling of the reservoir 112 via introduction of pre-vapor formulation into the reservoir 112 through at least the fluid port 114, thereby enabling pre-vapor formulation to be introduced into the reservoir 112 independently of the vaporizer assembly 130 and/or conduit 140.

Additionally, as noted above, the reservoir assembly 102 may be configured to enable supplying of pre-vapor formulation from reservoir 112 to the vaporizer assembly 130 via fluid port 134, to enable the vaporizer assembly 130 to generate a vapor based on the heater 136 heating at least a portion of pre-vapor formulation supplied to the vaporizer assembly 130 from the reservoir 112.

Still referring to FIGS. 1A-1B, the isolation structure 116 is configured to move (e.g., is configured to be movable) in relation to both the reservoir 112 and the vaporizer assembly 130 to expose fluid port 114 while covering fluid port 134, to cover fluid port 114 while exposing fluid port 134, and/or to cover both the fluid port 114 and the fluid port 134 at the same time. In some example embodiments, isolation structure 116 cannot cover both the fluid port 114 and the fluid port 134 at the same time. In some example embodiments, the isolation structure 116 may be movable to expose either the fluid port 114 or the fluid port 134, but not both at a given time. In some example embodiments, the isolation structure 116 is configured to preclude simultaneous exposure of fluid port 114 and fluid port 134. In some example embodiments, the isolation structure 116 is configured to move to cover both the fluid port 114 and the fluid port 134 at the same time. In some example embodiments, fluid port 114 may include more than one port (e.g., there may be multiple fluid ports 114), and/or fluid port 134 may include more than one port (e.g., there may be multiple fluid ports 134), and the functionality described above can similarly apply. For example, the isolation structure 116 may be configured to move to expose the one or more fluid ports 114 while covering the one or more fluid ports 134, to cover the one or more fluid ports 114 while exposing the one or more fluid ports 134, and/or to cover the one or more fluid ports 114 and the one or more fluid ports 134 at the same time.

In some example embodiments, the isolation structure 116 is configured to move to expose the reservoir 112 to either an exterior of the reservoir 112 via fluid port 114, or to the vaporizer assembly 130 via fluid port 134, both not both at a given time, for example, to isolate the reservoir 112 from the vaporizer assembly 130 based on covering fluid port 134 while exposing fluid port 114, and thereby enabling refilling of the reservoir 112 through fluid port 114 while precluding transfer of pre-vapor formulation from the reservoir 112 to the vaporizer assembly 130, or for example, to expose the reservoir 112 to the vaporizer assembly 130 by exposing fluid port 134 while covering fluid port 114, thereby isolating the reservoir 112 from an exterior of the reservoir 112 via fluid port 114 while enabling pre-vapor formulation to be drawn from the reservoir 112 to the vaporizer assembly 130 to enable generation of a vapor at the vaporizer assembly 130 based on heating the drawn pre-vapor formulation while precluding transfer of pre-vapor formulation between the reservoir 112 and an exterior of the reservoir 112 via fluid port 114. In some example embodiments, the isolation structure 116 may be configured to cover both fluid port 114 and fluid port 134 simultaneously. In some example embodiments, fluid port 114 may include more than one port (e.g., there may be multiple fluid ports 114), and/or fluid port 134 may include more than one port (e.g., there may be multiple fluid ports 134), and the functionality described above can similarly apply. For example, the isolation structure 116 may be configured to move to expose the reservoir 112 to either an exterior of the reservoir 112 via one or more fluid ports 114 while covering the one or more fluid ports 134, to expose the reservoir 112 to the vaporizer assembly 130 via the one or more fluid ports 134 while covering the one or more fluid ports 114, and/or to isolate the reservoir 112 from both the exterior of the reservoir 112 and the vaporizer assembly 130 by covering both the one or more fluid ports 114 and the one or more fluid ports 134 at the same time.

Still referring to FIGS. 1A-1B, an example power supply assembly 120 may include a power supply 122. The power supply 122 may be a rechargeable battery, and the power supply assembly 120 may be configured to supply electrical power from the power supply 122 to the vapor generator assembly 110 (e.g., to the heater 136 via one or more electrical leads) to support vapor generation at the vaporizer assembly 130.

As shown in FIG. 1B, an example e-vaping device 100 may include an instance of control circuitry 124 that may be configured to control the supply of electrical power from the power supply 122 to the vapor generator assembly 110 (e.g., to the vaporizer assembly 130). In the example embodiments shown in FIG. 1B, the control circuitry 124 is included in the power supply assembly 120, but it will be understood that, in some example embodiments, the control circuitry 124 may be included in the vapor generator assembly 110 instead of the power supply assembly 120. In some example embodiments, the e-vaping device 100 may be a unitary piece that includes the vapor generator assembly 110 and the power supply assembly 120 in the unitary piece, instead of including the vapor generator assembly 110 and the power supply assembly 120 as separate pieces that are coupled together to form the e-vaping device 100.

In some example embodiments, wherein the vapor generator assembly 110 and the power supply assembly 120 are configured to be detachably coupled via complementary connector assemblies 118 and 128, respectively, one or more electrical circuits through the vapor generator assembly 110 and the power supply assembly 120 may be established based on connector assemblies 118, 128 being coupled together. In one example, the one or more established electrical circuits may include at least the heater 136, the control circuitry 124, and the power supply 122. The electrical circuit may include one or more electrical leads in one or both of connector assemblies 118, 128. In some example embodiments, the e-vaping device 100 may be a unitary piece that includes the vapor generator assembly 110 and the power supply assembly 120 in the unitary piece, such that there is no need to couple the vapor generator assembly 110 and the power supply assembly 120 together to establish the one or more electrical circuits.

In some example embodiments, the power supply 122 may include a battery. In some examples, the power supply 122 may include a Lithium-ion battery or one of its variants, for example a Lithium-ion polymer battery, or a different type of battery. Further, the power supply 122 may be rechargeable and may include circuitry configured to allow the battery to be chargeable by an external charging device.

In some example embodiments, the power supply 122 may be electrically connected with the heater 136 by control circuitry 124 based on a signal received at the control circuitry 124 from a sensor of the e-vaping device 100, an interface of the e-vaping device 100, or a combination thereof. To control the supply of electrical power to a heater 136, the control circuitry 124 may execute one or more instances of computer-executable program code. The control circuitry 124 may include a processor and a memory. The memory may be a computer-readable storage medium storing computer-executable code. The control circuitry 124 may be a special purpose machine configured to execute the computer-executable code to control the supply of electrical power to the heater 136.

In some example embodiments, connector assemblies 118, 128 are omitted from the e-vaping device 100, such that the vapor generator assembly 110 and the power supply assembly 120 are fixedly coupled together (e.g., are integral to each other) and are precluded from being detachably coupled with each other. As shown in FIGS. 1A and 1B, in some example embodiments, the outer housing 111 of the vapor generator assembly 110 and the outer housing 121 of the power supply assembly 120 may include a unitary piece of material.

A pre-vapor formulation is a material or combination of materials that may be transformed into a vapor. The reservoir 112, in some example embodiments, may include a storage medium that may hold a pre-vapor formulation. In some example embodiments, the dispensing interface 137 may include a wick, also referred to herein as an instance of wicking material. The dispensing interface 137 may include filaments (or threads) having a capacity to draw the pre-vapor formulation, although example embodiments are not limited thereto and any other type of wicking materials may be used. In some example embodiments, the heater 136 may include a wire coil, although example embodiments are not limited thereto and any other type of heater may be used. A wire coil may at least partially surround the dispensing interface 137 in the interior space 135 of the vaporizer assembly 130. The wire may be a metal wire and/or the wire coil may extend fully or partially along the length of the dispensing interface 137. The heater 136 may be formed of any suitable electrically resistive materials. The dispensing interface 137 may include one or more elements, including for example, a first wicking material and a second wicking material, wherein for example, a pre-vapor formulation may first wick through the first wicking material to get to the second wicking material, and the heater is configured to heat the pre-vapor formulation in the second wicking material.

In some example embodiments, one or more portions of the vapor generator assembly 110 may be replaceable. Such one or more portions may include the vaporizer assembly 130, the reservoir 112, the reservoir assembly 102, a sub-combination thereof, or a combination thereof. In some example embodiments, the entire e-vaping device 100 may be disposed once the reservoir 112, the vaporizer assembly 130, or a combination thereof is depleted.

The exterior of at least the reservoir 112 may include an exterior of the reservoir 112, an exterior of the reservoir assembly 102, an exterior of the vapor generator assembly 110, an exterior of the e-vaping device 100, a sub-combination thereof, or a combination thereof. Accordingly, an exterior of at least the reservoir 112 may include an external environment that is external to the reservoir 112, an external environment that is external to the reservoir assembly 102, an external environment that is external to the vaporizer assembly 130, an external environment that is external to the vapor generator assembly 110, an external environment that is external to the e-vaping device 100, a sub-combination thereof, or a combination thereof.

In some example embodiments, the reservoir assembly 102 may include a vaporizer assembly connector that is configured to detachably couple the reservoir 112 with the vaporizer assembly 130. The fluid port 134 may extend through the vaporizer connector assembly to enable fluid communication between the reservoir 112 and an exterior of at least the reservoir 112 through the vaporizer connector assembly. In some example embodiments, the vaporizer assembly 130 is integral to the vapor generator assembly 110, such that the vaporizer assembly 130 and the reservoir assembly 102 are fixedly coupled together and are precluded from detachably coupling with each other and the outer housing 111 of the reservoir 112 and the outer housing 131 of the vaporizer assembly 130 are at least partially collectively defined by a unitary piece of material.

Figure 2B:
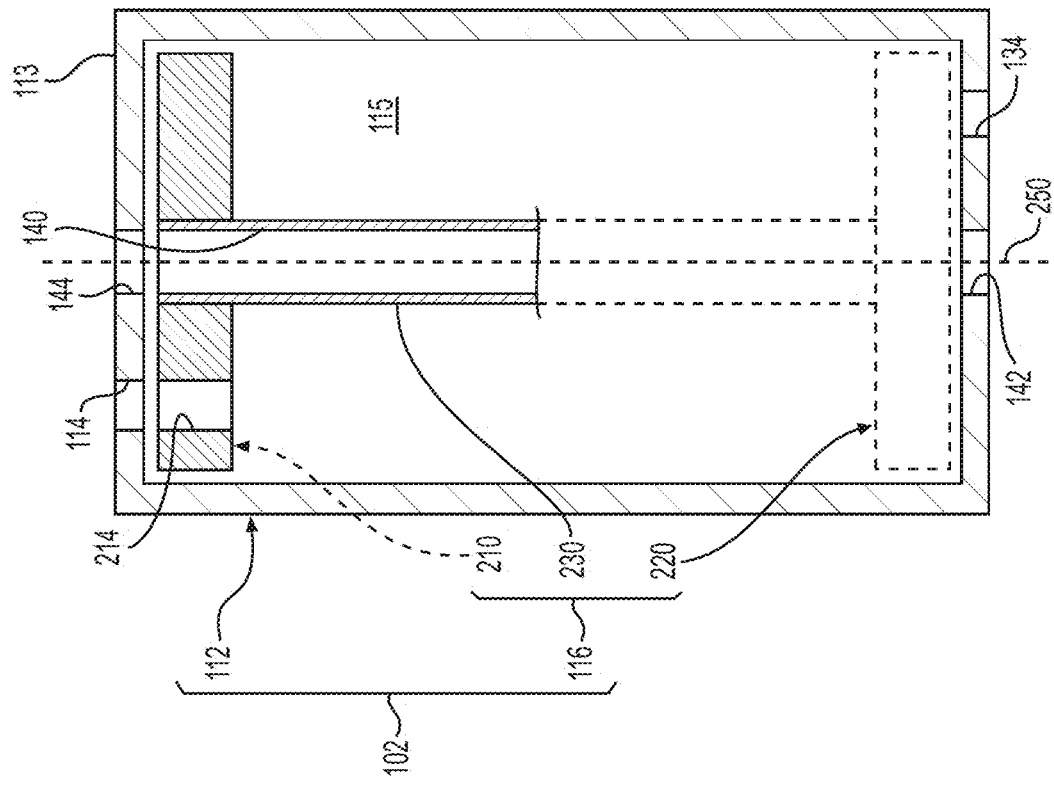
FIG. 2B is a cross-sectional view along line IIB-IIB' of the reservoir assembly of FIG. 2A according to some example embodiments.
Figure 2A:
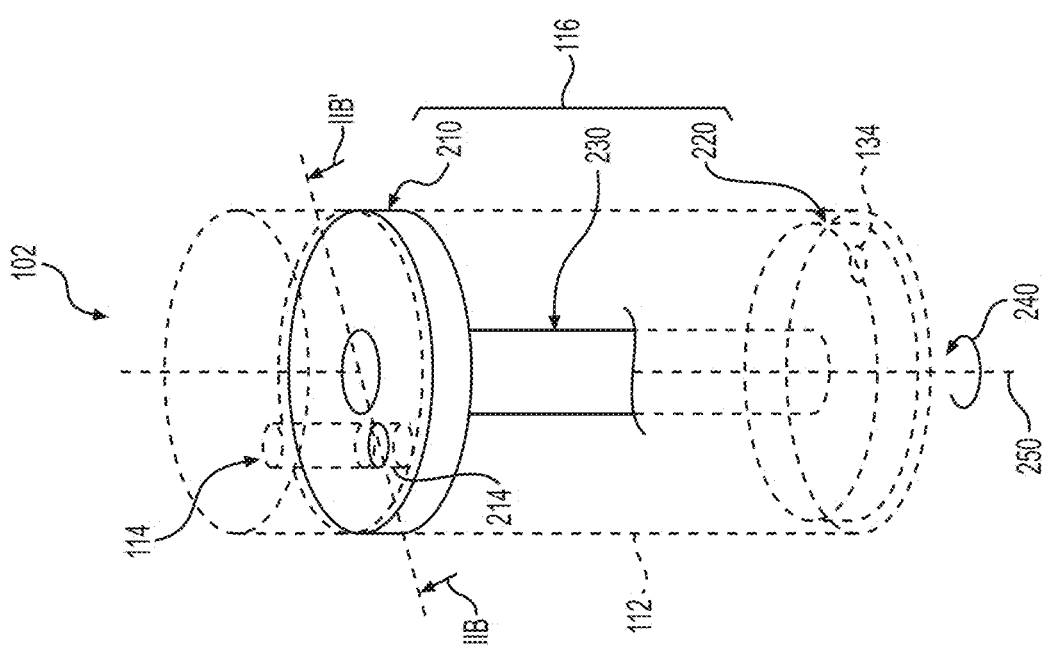
FIG. 2A is a perspective view of a reservoir assembly according to some example embodiments.
Figure 4B:
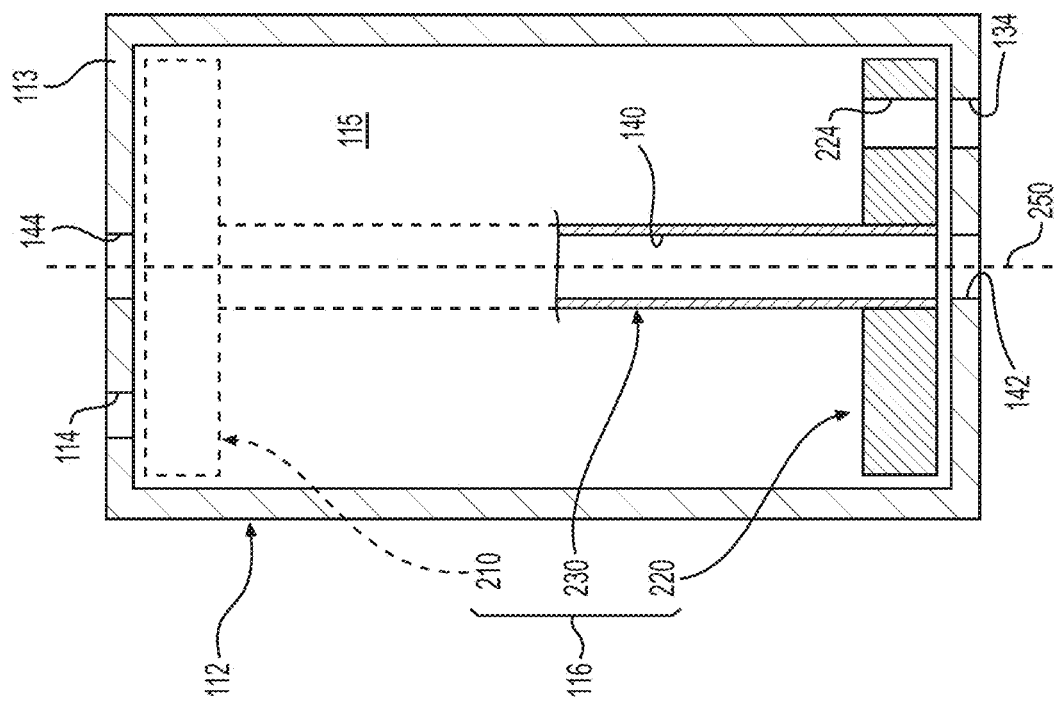
FIG. 4B is a cross-sectional view along line IVB-IVB' of the reservoir assembly of FIG. 4A according to some example embodiments.
Figure 4A:
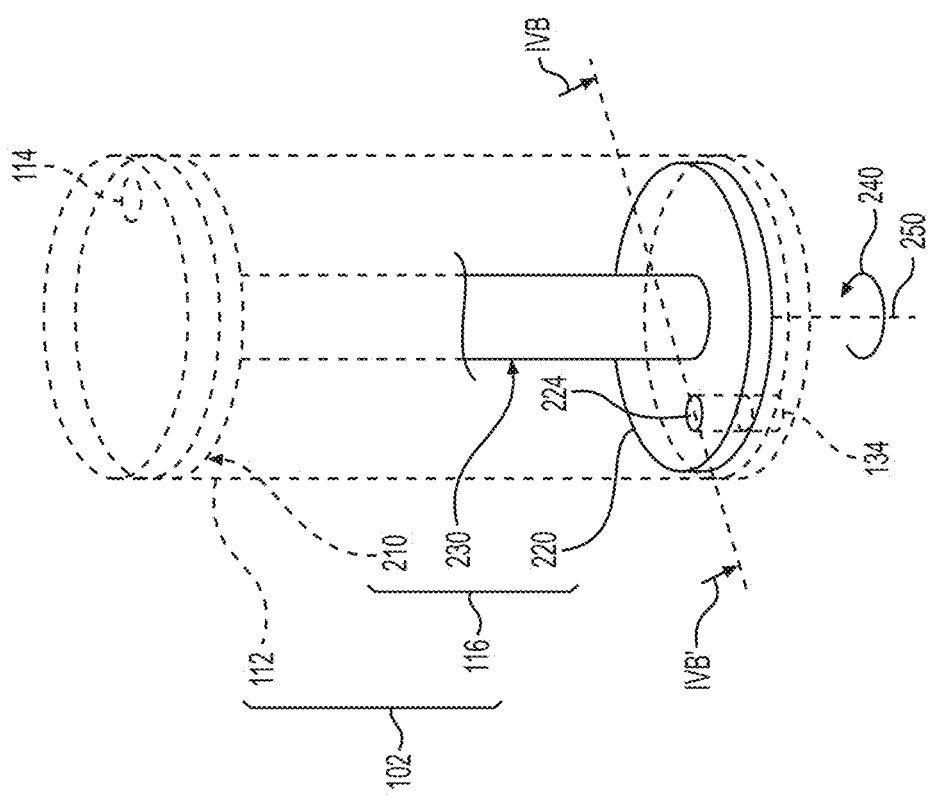
FIG. 4A is a perspective view of a reservoir assembly according to some example embodiments.
Figures 5A, 5B:
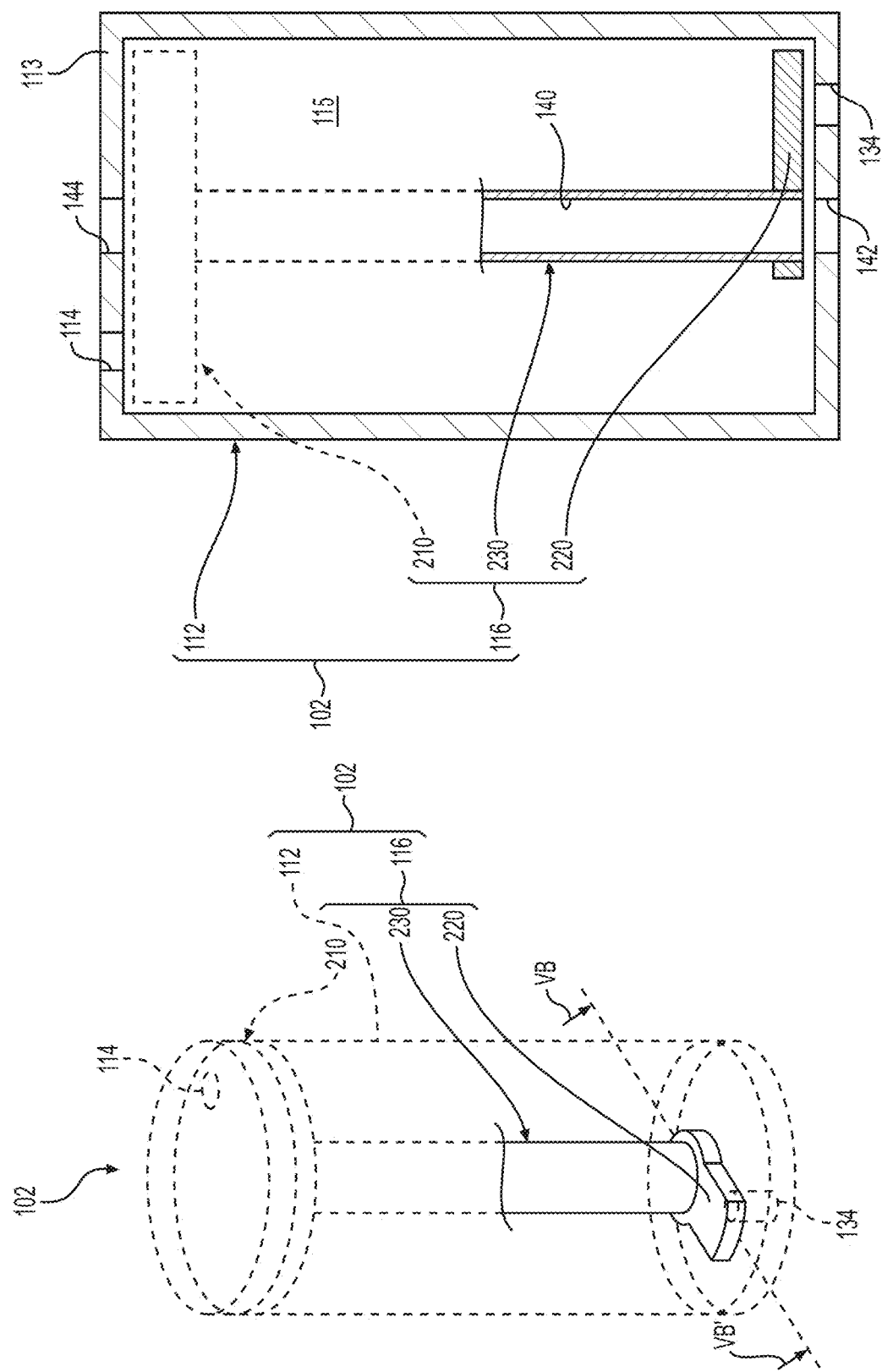
FIG. 5A is a perspective of a reservoir assembly according to some example embodiments.
FIG. 5B is a cross-sectional view along line VB-VB' of the reservoir assembly of FIG. 5A according to some example embodiments.

FIG. 2A is a perspective view of a reservoir assembly 102 according to some example embodiments. FIG. 2B is a cross-sectional view along line IIB-IIB' of the reservoir assembly 102 of FIG. 2A according to some example embodiments. FIG. 3A is a perspective of a reservoir assembly 102 according to some example embodiments. FIG. 3B is a cross-sectional view along line IIIB-IIIB' of the reservoir assembly 102 of FIG. 3A according to some example embodiments. FIG. 4A is a perspective view of a reservoir assembly 102 according to some example embodiments. FIG. 4B is a cross-sectional view along line IVB-IVB' of the reservoir assembly 102 of FIG. 4A according to some example embodiments. FIG. 5A is a perspective of a reservoir assembly 102 according to some example embodiments. FIG. 5B is a cross-sectional view along line VB-VB' view of the reservoir assembly 102 of FIG. 5A according to some example embodiments.

In some example embodiments, an isolation structure 116 of a reservoir assembly 102 includes multiple structures that are coupled together to form the isolation structure 116, or one structure with different parts (e.g., while reference is made to one or more structures, one or more of these could form part of the same structure). The isolation structure 116 may include a first structure 210 and a second structure 220. The first structure 210 may be configured to move to either expose or cover the fluid port 114. The second structure 220 may be configured to move to either expose or cover the fluid port 134. The isolation structure 116 may further include a coupling structure 230 that couples the first structure 210 and the second structure 220 together, such that movement of the isolation structure 116 includes movement of the first structure 210 together with the second structure 220 in unison via the coupling structure 230. As shown in FIGS. 2A-3B, the coupling structure 230 may be a hollow structure that encloses at least a portion of conduit 140 within an interior thereof, but it will be understood that example embodiments are not limited thereto. As shown in FIGS. 1A-1B, one or more portions of the isolation structure 116 may be coupled to an interface assembly 117 so that the isolation structure 116 is configured to move based on manual (e.g., adult vaper) manipulation of the interface assembly 117.

In some example embodiments, the isolation structure 116 may omit the first or second structures 210, 220. In some example embodiments, for example where the isolation structure 116 includes the second structure 220 but omits the first structure 210, the second structure 220 may be referred to as a "first structure" of the isolation structure 116. Even when both structures 210, 220 are included, the structures should not be limited by the terms "first," "second," etc. As noted already, the terms "first," "second," etc. are only used to distinguish one element or structure from another, and thus, a first structure could be termed a second structure, and vice-versa.

In FIGS. 2A-2B and FIGS. 3A-3B, the isolation structure 116 is illustrated such that example embodiments of the first structure 210 are shown in detail and the second structure 220 is shown in the abstract through a dashed-line representation, while FIGS. 4A-4B and FIGS. 5A-5B illustrate the isolation structure such that example embodiments of the second structure 220 are shown in detail and the first structure 210 is shown in the abstract through a dashed-line representation, to show that an isolation structure 116 of FIGS. 2A-3B may include any example embodiment of a second structure 220 (e.g., including any of the example embodiments of a second structure 220 shown in FIGS. 4A-5B), including an omission of a second structure 220 from the isolation structure 116, and an isolation structure 116 of FIGS. 4A-5B may include any example embodiment of a first structure 210 (e.g., including any of the example embodiments of a first structure 210 shown in FIGS. 2A-3B), including an omission of a first structure 210 from the isolation structure 116.

Referring first to some example embodiments, including the example embodiments shown in FIGS. 2A-2B, an isolation structure 116 may include a first structure 210 and a second structure 220 coupled via a coupling structure 230, where the first structure 210 is a disc structure that includes a fluid port 214 extending through the disc structure of the first structure 210. The isolation structure 116 may be configured to move (e.g., based on rotating 240 the isolation structure 116 around a longitudinal axis 250 of the isolation structure 116) to move first structure 210 to adjustably align or at least partially align fluid port 214 with fluid port 114 or to cover fluid port 114 with the disc structure of first structure 210, such that the first structure 210 either exposes fluid port 114 based on fluid port 214 at least partially aligning with fluid port 114 or isolates fluid port 114 through the disc structure of the first structure 210. Thus, the isolation structure 116 may expose the reservoir 112 to, or isolate the reservoir 112 from, an exterior of at least the reservoir 112 through fluid port 114 based on isolation structure 116 moving to adjustably align or mis-align fluid port 214 of the first structure 210 with fluid port 114.

Referring now to some example embodiments, including the example embodiments shown in FIGS. 3A-3B, an isolation structure 116 may include a first structure 210 and a second structure 220 coupled via a coupling structure 230, where the first structure 210 is a protrusion structure that is configured to isolate the fluid port 114 based on the protrusion structure covering the fluid port 114. The isolation structure 116 may be configured to move (e.g., based on rotating 240 the isolation structure 116 around a longitudinal axis 250 of the isolation structure 116) to move the protrusion structure 210 to adjustably cover fluid port 114 or to at least partially expose fluid port 114, such that the first structure 210 either isolates fluid port 114, or exposes fluid port 114. Thus, the isolation structure 116 may expose the reservoir 112 to, or isolate the reservoir 112 from, an exterior of at least the reservoir 112 through fluid port 114 based on isolation structure 116 moving to adjustably mis-align or align first structure 210 with fluid port 114.

It will be understood that the first structure 210, the second structure 220, and the coupling structure 230 may be included in a common structure to form the isolation structure 116. The common structure may be a unitary piece of material.

Referring now to some example embodiments, including the example embodiments shown in FIGS. 4A-4B, an isolation structure 116 may include a first structure 210 and a second structure 220 coupled via a coupling structure 230, where the second structure 220 is a disc structure that includes a fluid port 224 extending through the disc structure of the second structure 220.

The isolation structure 116 may be configured to move (e.g., based on rotating 240 the isolation structure 116 around a longitudinal axis 250 of the isolation structure 116) to move second structure 220 to adjustably align or at least partially align fluid port 224 with fluid port 134 or to cover fluid port 134 with the disc structure of second structure 220, such that the second structure 220 either exposes fluid port 134 based on fluid port 224 at least partially aligning with fluid port 134 or isolates fluid port 134 through the disc structure of the second structure 220. Thus, the isolation structure 116 may expose the reservoir 112 to, or isolate the reservoir 112 from, an exterior of at least the reservoir 112 through fluid port 134 based on isolation structure 116 moving to adjustably align or mis-align fluid port 224 of the second structure 220 with fluid port 134.

Referring now to some example embodiments, including the example embodiments shown in FIGS. 5A-5B, an isolation structure 116 may include a first structure 210 and a second structure 220 (coupled via a coupling structure 230, where the second structure 220 is a protrusion structure that is configured to isolate the fluid port 134 based on the protrusion structure covering the fluid port 134. The isolation structure 116 may be configured to move (e.g., based on rotating 240 the isolation structure 116 around a longitudinal axis 250 of the isolation structure 116) to move the protrusion structure 220 to adjustably cover fluid port 134 or to at least partially expose fluid port 134, such that the second structure 220 either isolates fluid port 134, or exposes fluid port 134. Thus, the isolation structure 116 may expose the reservoir 112 to, or isolate the reservoir 112 from, an exterior of at least the reservoir 112 through fluid port 134 based on isolation structure 116 moving to adjustably mis-align or align second structure 220 with fluid port 134.

Figure 6A:
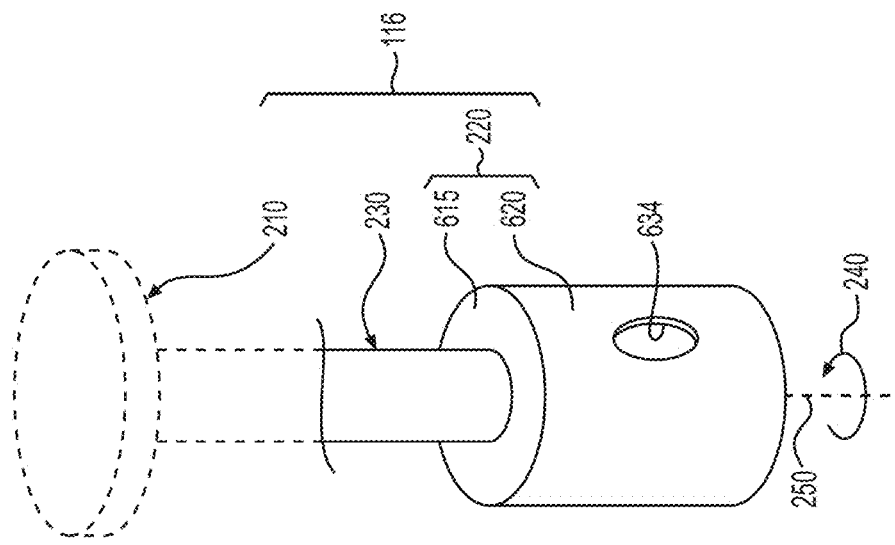
FIG. 6A is a cross-sectional view of a vapor generator assembly according to some example embodiments.
Figure 6B:
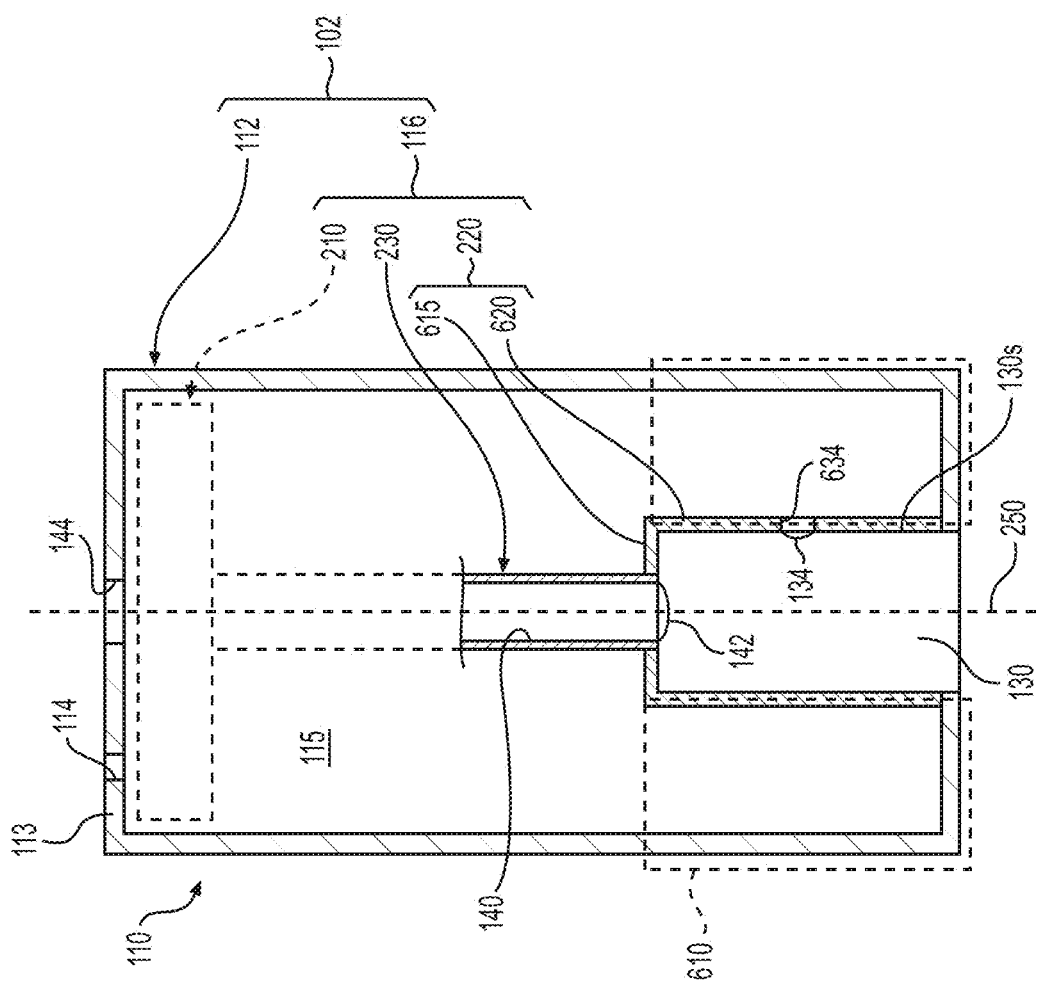
FIG. 6B is a perspective view of the isolation structure of FIG. 6A according to some example embodiments.

FIG. 6A is a cross-sectional view of a vapor generator assembly according to some example embodiments. FIG. 6B is a perspective view of the isolation structure of FIG. 6A according to some example embodiments.

In FIGS. 6A-6B, the isolation structure 116 is illustrated such that example embodiments of the second structure 220 are shown in detail and the first structure 210 is shown in the abstract through a dashed-line representation, to show that the isolation structure 116 of FIGS. 6A-6B may include any example embodiment of a first structure 210.

In some example embodiments, the reservoir 112 is configured to at least partially surround the vaporizer assembly 130. For example, as shown in FIG. 6A, the reservoir 112 may include an annular portion 610 extending coaxially around the vaporizer assembly 130 along longitudinal axis 250. As further shown in FIG. 6A, the fluid port 134 may extend, at least partially radially with respect into the longitudinal axis 250, through a side surface 130$s$ of the vaporizer assembly 130, to the annular portion 610.

As further shown in FIGS. 6A-6B, the isolation structure 116 may include a second structure 220 that includes a cylindrical structure 620 that extends coaxially around the vaporizer assembly 130 along the longitudinal axis 250, such that the cylindrical structure 620 is between the vaporizer assembly 130 and the annular portion 610. As shown in FIGS. 6A-6B, the second structure 220 may also include a disc structure 615, and the cylindrical structure 620 may extend coaxially from the disc structure 615, but example embodiments are not limited thereto. As shown in FIGS. 6A-6B, second structure 220 may include a fluid port 634 that extends through the cylindrical structure 620. The cylindrical structure 620 may be configured to align fluid port 634 with fluid port 134 based on the cylindrical structure 620 being rotated 240 around the longitudinal axis 250. Accordingly, the isolation structure 116 may be configured to be moved (e.g., based on rotating 240 the isolation structure 116 around the longitudinal axis 250, which may be a longitudinal axis of the isolation structure 116) to rotate the cylindrical structure 620 around the longitudinal axis 250 to thus rotate the cylindrical structure 620 around the side surface 130$s$ of the vaporizer assembly 130 to adjustably align or at least partially align fluid port 634 with fluid port 134 or to mis-align fluid port 634 with fluid port 134 such that the cylindrical structure 620 covers the fluid port 134, such that the second structure 220 either exposes fluid port 134 through at least partially-aligned fluid port 634 or isolates fluid port 134 through the cylindrical structure 620 of the second structure 220. Thus, the isolation structure 116 may expose the reservoir 112 to, or isolate the reservoir 112 from, the vaporizer assembly 130 through fluid port 134 based on the isolation structure 116 moving to adjustably align or mis-align fluid port 634 with fluid port 134. In some example embodiments, structures 620 and 615 may be separate structures joined together, and in some example embodiments structures 620 and 615 may form part of the same structure, which may be a unitary piece of material.

Figure 7B:
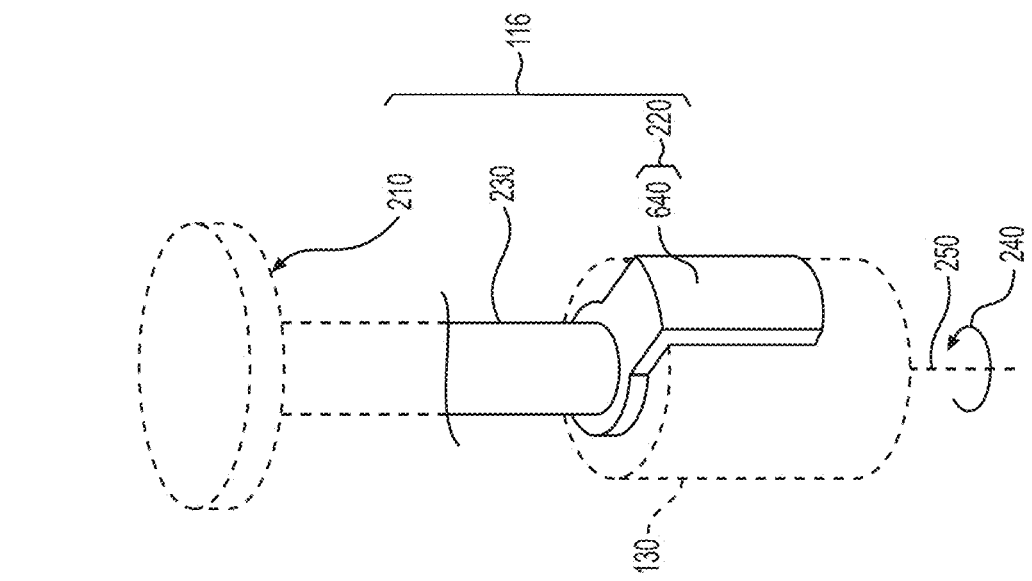
FIG. 7B is a perspective view of the isolation structure of FIG. 7A according to some example embodiments.
Figure 7A:
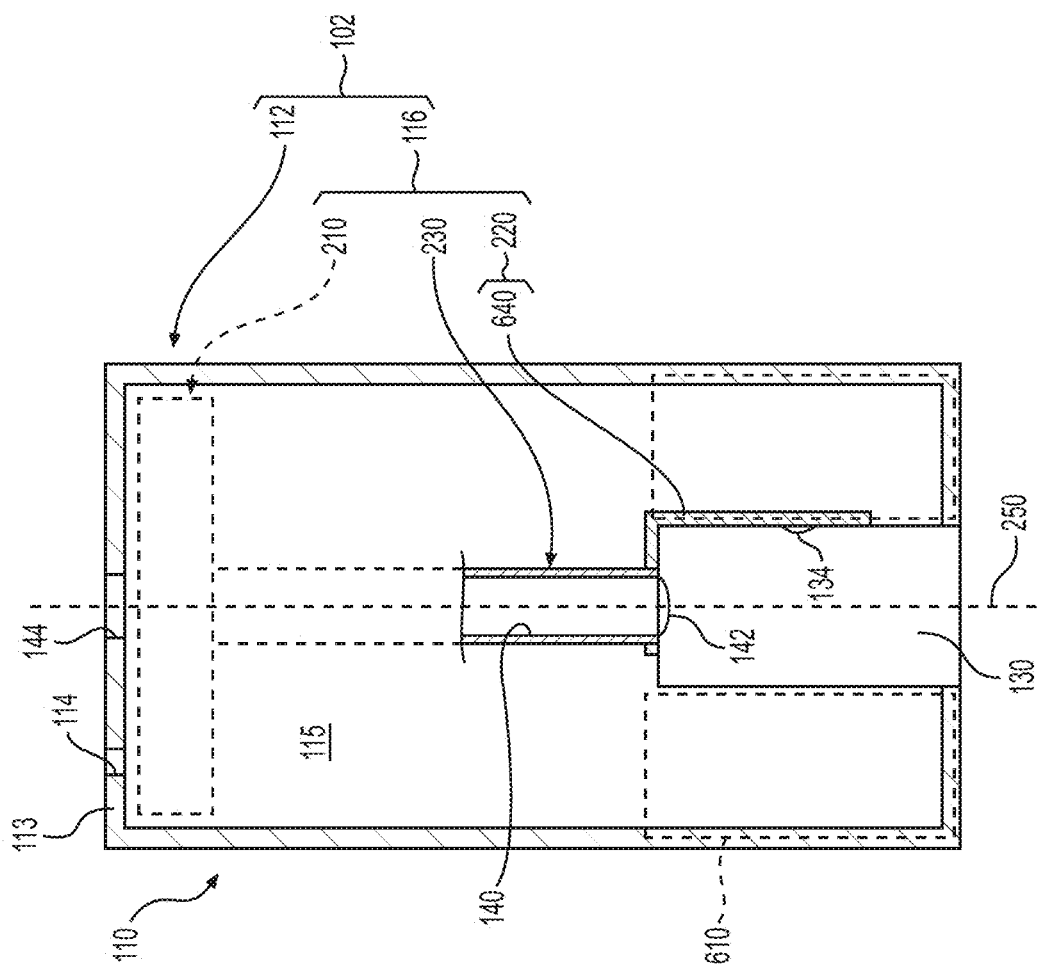
FIG. 7A is a cross-sectional view of a vapor generator assembly according to some example embodiments.

FIG. 7A is a cross-sectional view of a vapor generator assembly according to some example embodiments. FIG. 7B is a perspective view of the isolation structure of FIG. 7A according to some example embodiments.

In FIGS. 7A-7B, the isolation structure 116 is illustrated such that example embodiments of the second structure 220 are shown in detail and the first structure 210 is shown in the abstract through a dashed-line representation, to show that the isolation structure 116 of FIGS. 7A-7B may include any example embodiment of the first structure 210.

In some example embodiments, the reservoir 112 is configured to at least partially surround the vaporizer assembly 130. For example, as shown in FIG. 7A, the reservoir 112 may include an annular portion 610 extending coaxially around the vaporizer assembly 130. As further shown in FIG. 7A, the fluid port 134 may extend through a side surface of the vaporizer assembly 130, at least partially radially with respect into the longitudinal axis 250, to the annular portion 610.

As further shown in FIGS. 7A-7B, the isolation structure 116 may include a second structure that includes a cylindrical protrusion structure 640 that extends coaxially around at least a portion of the vaporizer assembly 130 along longitudinal axis 250, such that the cylindrical protrusion structure 640 is between the vaporizer assembly 130 and the annular portion 610. As shown in FIGS. 7A-7B, the cylindrical protrusion structure 640 may be configured to be adjustably aligned or mis-aligned with fluid port 134 based on the isolation structure 116 being rotated 240 around the longitudinal axis 250. Accordingly, the isolation structure 116 may be configured to be moved (e.g., based on rotating 240 the isolation structure 116 around the longitudinal axis 250) to rotate the cylindrical protrusion structure 640 around the longitudinal axis 250 to be adjustably aligned or mis-aligned with fluid port 134, such that the second structure 220 either covers fluid port 134 or exposes fluid port 134. Thus, the isolation structure 116 may expose the reservoir 112 to, or isolate the reservoir 112 from, the vaporizer assembly 130 through fluid port 134 based on the isolation structure 116 moving to adjustably mis-align or align cylindrical protrusion structure 640 with fluid port 134.

Figure 8:
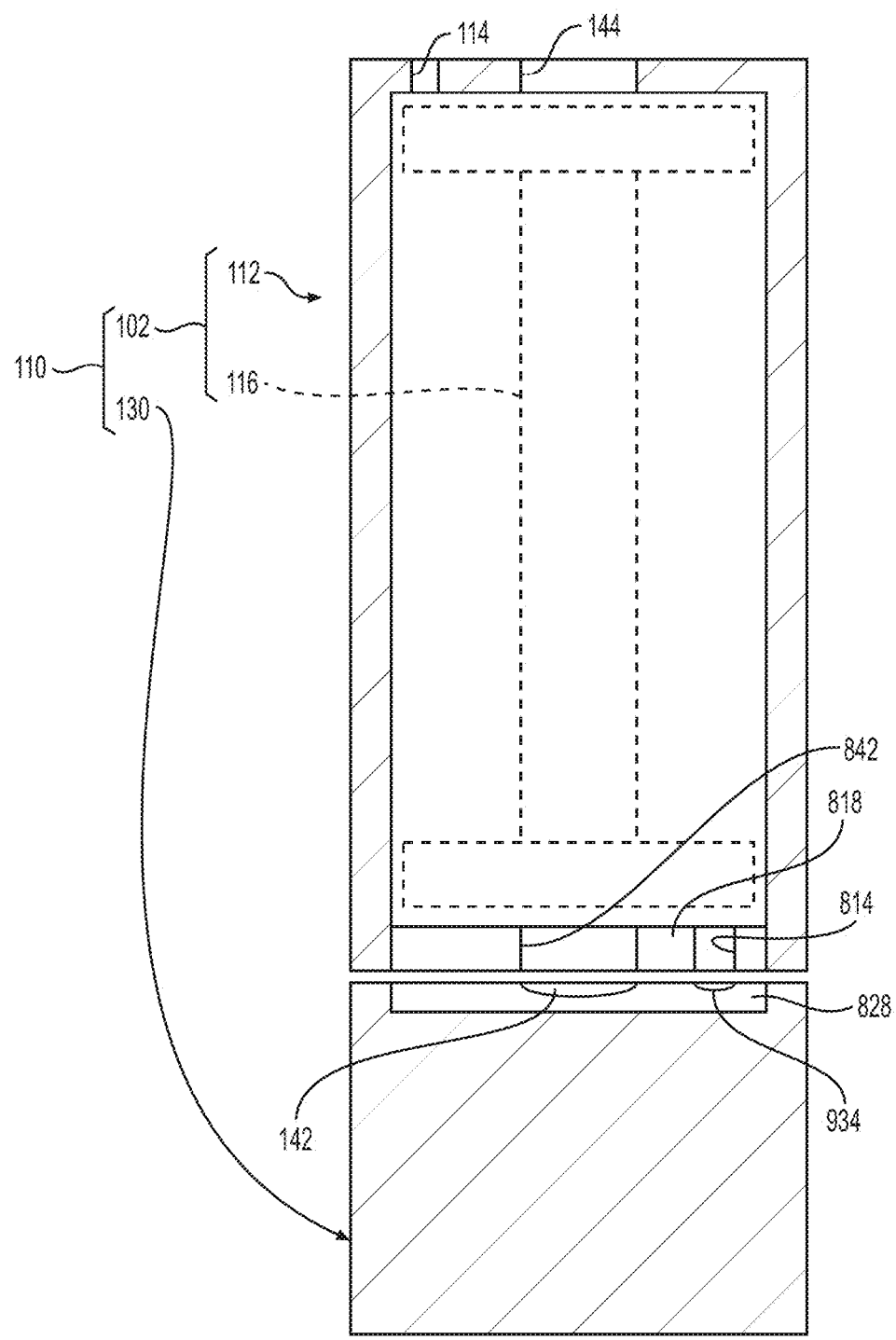
FIG. 8 is a cross-sectional view of a vapor generator assembly according to some example embodiments.
Figure 9:
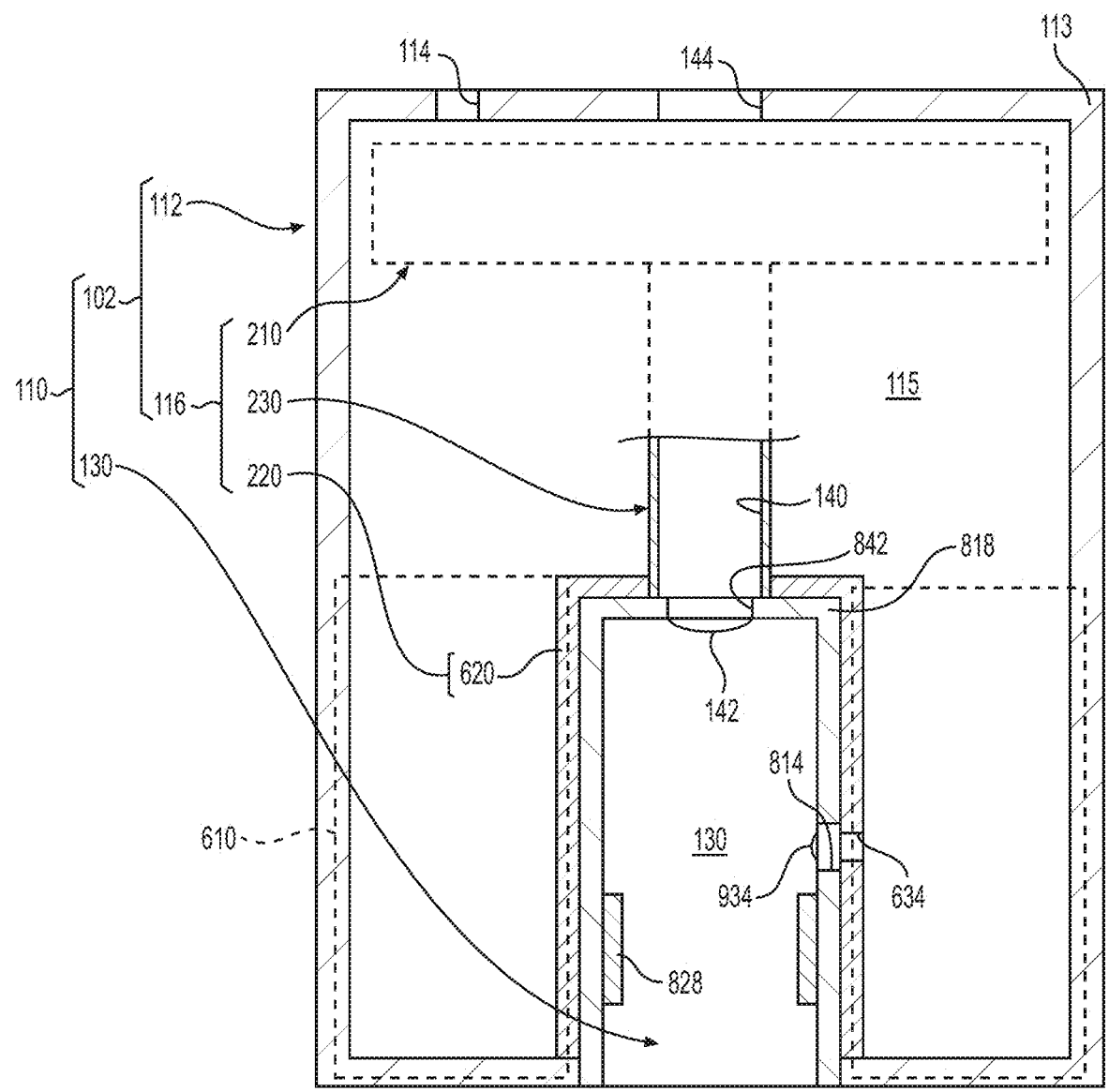
FIG. 9 is a cross-sectional view of a vapor generator assembly according to some example embodiments.

FIG. 8 is a cross-sectional view of a vapor generator assembly according to some example embodiments. FIG. 9 is a cross-sectional view of a vapor generator assembly according to some example embodiments. In FIGS. 8-9, the isolation structure 116 is shown in the abstract through a dashed-line representation, to show that the isolation structure 116 of FIGS. 8-9 may include any example embodiment of the isolation structure 116.

In some example embodiments, a reservoir assembly 102 that includes a reservoir 112 and isolation structure 116 is configured to be detachably coupled to a vaporizer assembly 130 to form a vapor generator assembly 110. As shown in FIGS. 8-9, the reservoir assembly 102 may include, in addition to the reservoir 112 and isolation structure 116, a vaporizer connector assembly 818 that is configured to detachably connect with a connector assembly 828 of a vaporizer assembly 130 to detachably couple the reservoir 112 to the vaporizer assembly 130 to thus configure the reservoir 112 to supply pre-vapor formulation to the vaporizer assembly 130, and to thus configure the vaporizer assembly 130 to draw pre-vapor formulation from the reservoir 112. As shown, the vaporizer connector assembly 818 may include a fluid port 814 extending through the vaporizer connector assembly 818 from the reservoir 112 to an exterior of at least the reservoir 112 through the vaporizer connector assembly 818.

In some example embodiments, the connector assemblies 818, 828 include threaded connectors. It should be appreciated that a connector assembly 818, 828 may be any type of connector, including, without limitation, a snug-fit, detent, clamp, bayonet, sliding fit, sleeve fit, alignment fit, threaded connector, magnetic, clasp, or any other type of connection, and/or combinations thereof.

As shown in FIGS. 8-9, the vaporizer assembly 130 may include a fluid port 934 that is configured to establish fluid communication between one or more elements of the vaporizer assembly (e.g., a heater 136 via a dispensing interface 137 of the vaporizer assembly 130) and an exterior of the vaporizer assembly 130. The vaporizer connector assembly 818 may be configured to detachably couple with the connector assembly 828 of the vaporizer assembly 130 such that the fluid port 934 of the vaporizer assembly 130 is aligned with the fluid port 814 of the vaporizer connector assembly, thereby configuring the fluid port 814 of the vaporizer connector assembly 818 to enable fluid communication between the reservoir 112 and the coupled vaporizer assembly 130 through the vaporizer connector assembly 818. As further shown in FIGS. 8-9, the vaporizer connector assembly 818 may include an air outlet port 842 that is coupled to conduit 140 and is configured to be coupled in fluid communication with outlet port 142 based on detachably coupling of vaporizer connector assembly 818 with vaporizer assembly 130. Accordingly, as shown in FIGS. 8-9, the isolation structure 116 may be moved to exclusively expose either fluid port 114 or the aligned fluid ports 814, 934 to exclusively expose the reservoir 112 to either an exterior of at least the reservoir 112 via an exposed fluid port 114, to the vaporizer connector assembly 818, alone or in combination with a vaporizer assembly 130 detachably coupled to the vaporizer connector assembly 818 (e.g., via exposed aligned fluid ports 814, 934), or to neither the exterior of at least the reservoir 112 nor the vaporizer connector assembly 818.

Figures 10A, 10B, 10C:
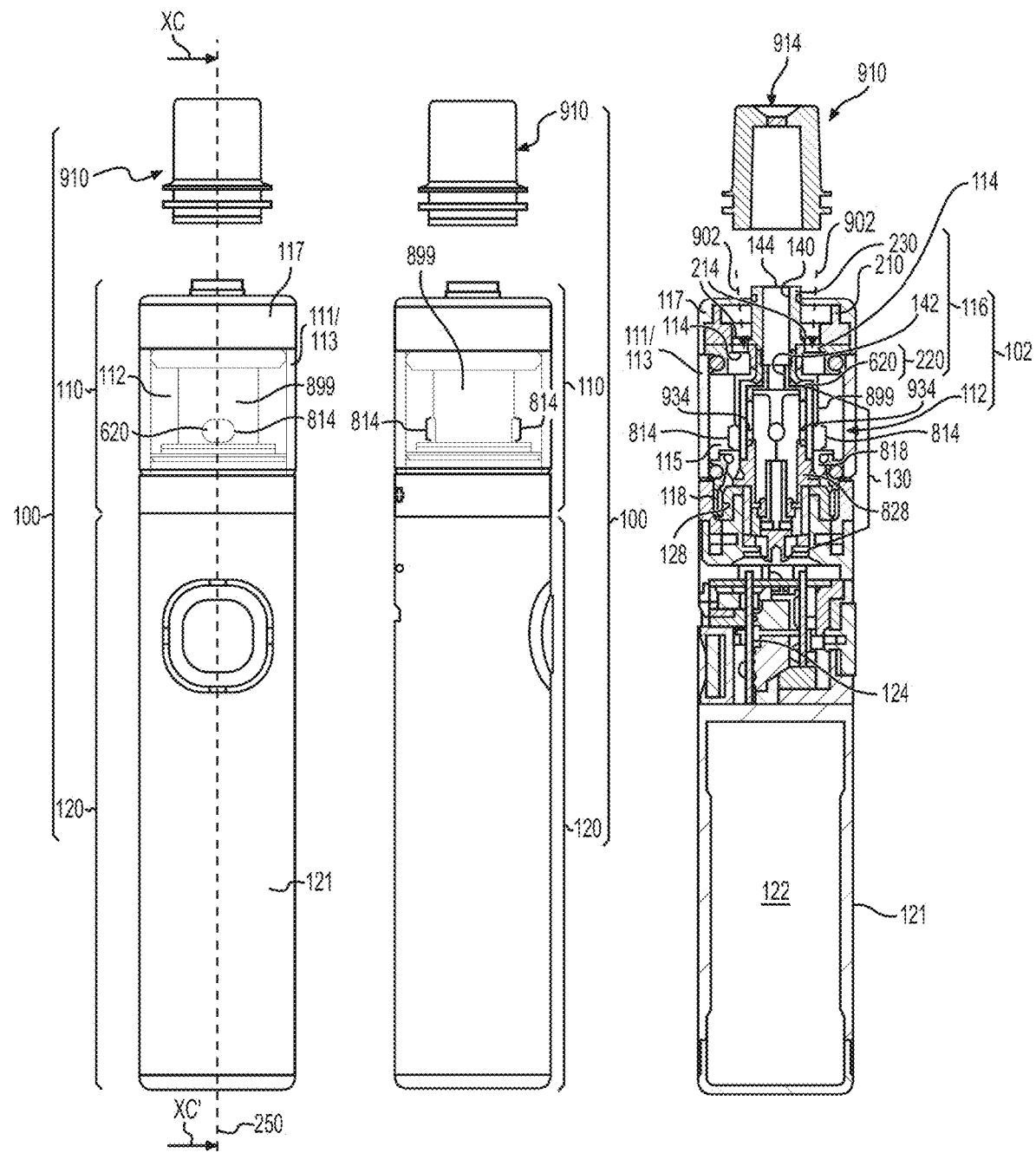
FIGS. 10A and 10B are side views of an e-vaping device according to some example embodiments.
FIG. 10C is a cross-sectional view along line XC-XC' of the e-vaping device of FIGS. 10A-10B according to some example embodiments.
Figure 10D:
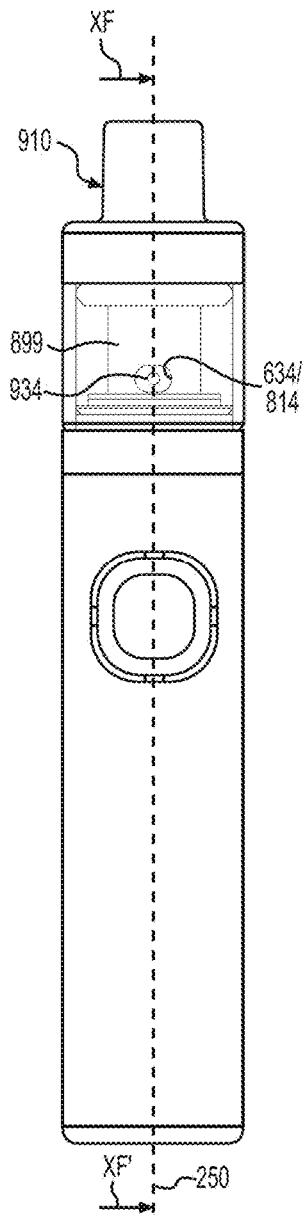
FIGS. 10D and 10E are side views of an e-vaping device according to some example embodiments.
Figure 10E:
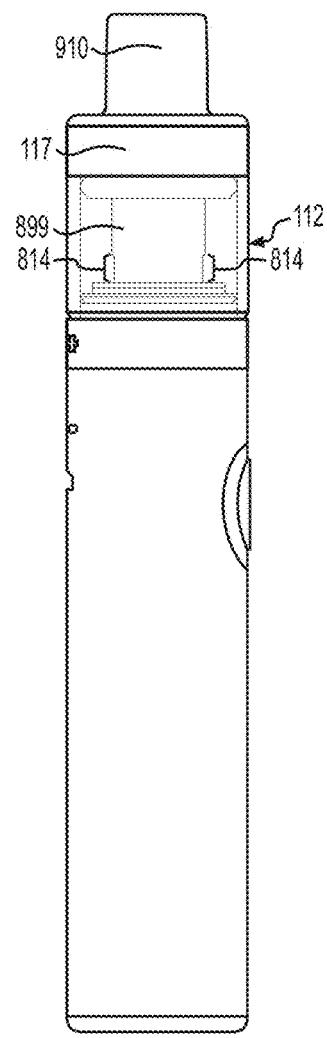
Figure 10F:
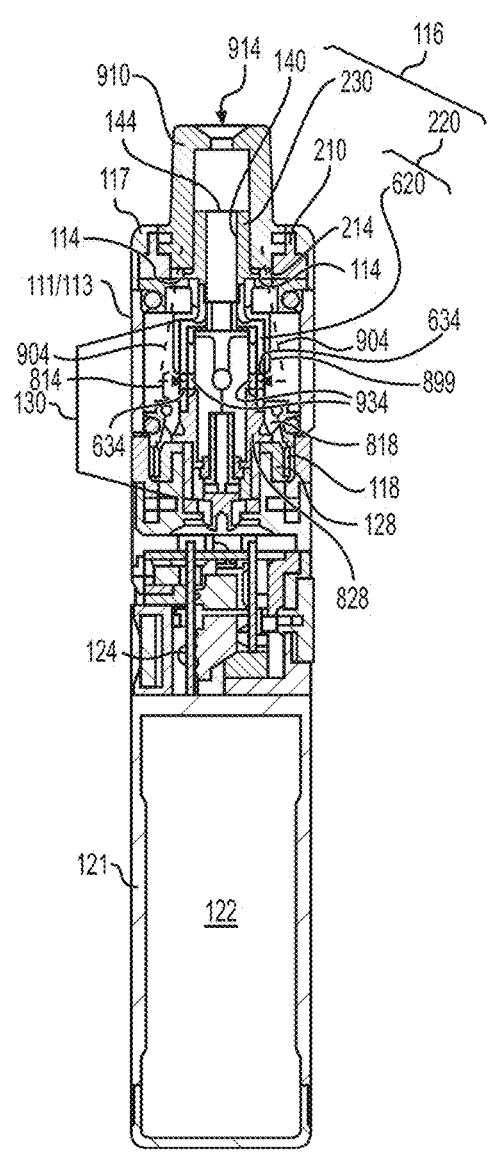
FIG. 10F is a cross-sectional view along line XF-XF' of the e-vaping device of FIGS. 10D-10E according to some example embodiments.
Figure 10H:
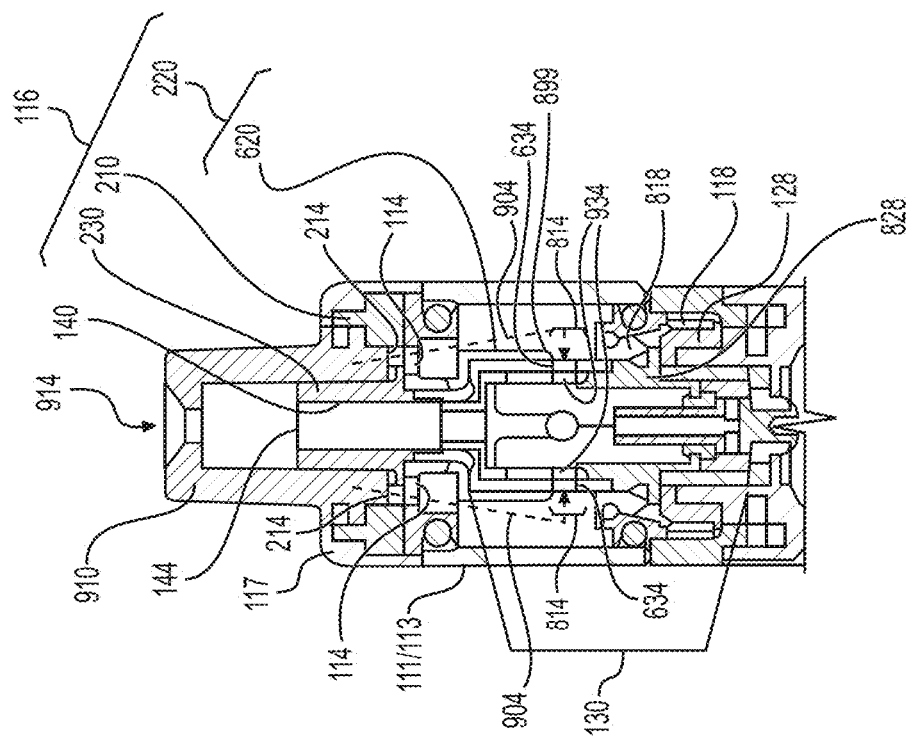
FIG. 10H is a cross-sectional view of a portion of the e-vaping device as shown in FIG. 10F according to some example embodiments.
Figure 10G:
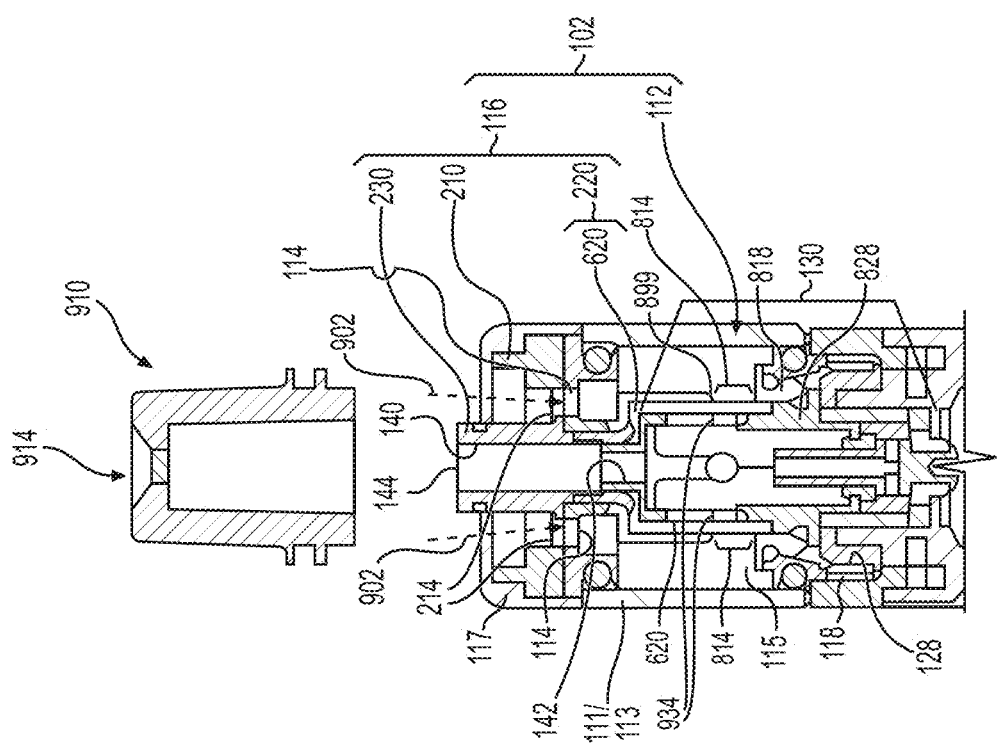
FIG. 10G is a cross-sectional view of a portion of the e-vaping device as shown in FIG. 10C according to some example embodiments.

FIGS. 10A and 10B are side views of an e-vaping device 100 according to some example embodiments. FIG. 10C is a cross-sectional view along line XC-XC' of the e-vaping device 100 of FIGS. 10A-10B according to some example embodiments. FIGS. 10D and 10E are side views of an e-vaping device 100 according to some example embodiments. FIG. 10F is a cross-sectional view along line XF-XF' of the e-vaping device 100 of FIGS. 10D-10E according to some example embodiments. FIG. 10G is a cross-sectional view of a portion of the e-vaping device as shown in FIG. 10C according to some example embodiments. FIG. 10H is a cross-sectional view of a portion of the e-vaping device as shown in FIG. 10F according to some example embodiments.

As shown in FIGS. 10A-10H, in some example embodiments, an e-vaping device may include a vapor generator assembly 110, a power supply assembly 120, and an outlet assembly 910. As shown, the vapor generator assembly 110 may include a connector assembly 118 and the power supply assembly 120 may include a connector assembly 128 that is complementary to connector assembly 118, where the vapor generator assembly 110 and the power supply assembly 120 may be detachably coupled with each other via coupling of connector assemblies 118, 128 with each other. Additionally, the vapor generator assembly 110 may include a reservoir assembly 102 and a vaporizer assembly 130 that are detachably coupled with each other via complementary connector assemblies 818, 828.

The reservoir assembly 102 includes a reservoir 112 having an outer housing 113 that at least partially defines the outer housing 111 of the vapor generator assembly 110 and an isolation structure 116. As shown in FIGS. 10A-10H, the isolation structure 116 includes a first structure 210, a coupling structure 230, and a second structure 220 that includes a cylindrical structure 620 with a fluid port 634 extending therethrough. As shown, the isolation structure 116 may be rotated around a longitudinal axis of the e-vaping device 100 to exclusively expose the reservoir 112 to either an exterior of at least the reservoir 112 via fluid port 114, at least the vaporizer assembly 130 via aligned fluid ports 634 and 934, or neither the exterior of at least the reservoir 112 nor the vaporizer assembly 130, based on the isolation structure 116 being moved to either align one or more fluid ports 214 of the first structure 210 with the one or more fluid ports 114 while covering the one or more fluid ports 934, align one or more fluid ports 634 with the one or more fluid ports 934 while covering the one or more fluid ports 114, or to align fluid ports 214, 634 with no fluid ports. As further shown, the isolation structure 116 is coupled to interface assembly 117 which is configured to be rotated (e.g., based on manual manipulation of the interface assembly 117) to cause the isolation structure 116 to be rotated around the longitudinal axis of the e-vaping device 100. As further shown in FIGS. 10A-10H, in some example embodiments, the first structure 210 may be located externally to the interior 115 of the reservoir 112, such that the one or more fluid ports 114 may be located between the interior 115 of the reservoir 112 and the first structure 210, and the coupling structure 230 may couple the first structure 210 that is located external to the reservoir 112 with the second structure 220 that is located within the interior 115 of the reservoir 112.

As further shown in FIGS. 10A-10H, the vaporizer connector assembly 818 may include a sheath 899 that extends through the interior space 115 of the reservoir 112 and defines a space within which the vaporizer assembly 130 is inserted when the vaporizer connector assembly 818 is coupled with the connector assembly 828 of the vaporizer assembly 130. As shown in at least FIGS. 10A-10H, the fluid port 814 of the vaporizer connector assembly 818 may extend, radially from the longitudinal axis 250, through the sheath 899. The vaporizer connector assembly 818 may be configured to couple with the connector assembly 828 of the vaporizer assembly 130 such that the fluid port 934 of the vaporizer assembly 130 is aligned with the fluid port 814 of the vaporizer connector assembly 818.

Referring now to FIGS. 10A-10C and 10G, based on the isolation structure 116 being moved (e.g., rotated around a longitudinal axis 250 based on manual manipulation of interface assembly 117) to at least partially align a fluid port 214 of the first structure 210 with a fluid port 114 of the reservoir 112, the reservoir 112 may be exposed to an exterior of at least the reservoir 112 through the aligned fluid ports 114, 214 such that a re-filling flow 902 of pre-vapor formulation may be introduced into the reservoir 112 from the exterior of at least the reservoir 112 via the aligned fluid ports 114, 214. As shown in FIGS. 10-10H, the vapor generator assembly 110 may include multiple fluid ports 114 and the isolation structure 116 may include multiple fluid ports 214 that correspond with the fluid ports 114, such that the isolation structure 116 may be moved to at least partially align the multiple fluid ports 214 with separate, respective fluid ports 114. In particular, as shown in FIGS. 10A-10H, the vapor generator assembly 110 may include two fluid ports 114 and the isolation structure 116 may include two fluid ports 214.

Referring now to FIGS. 10D-10F and 10H, based on the isolation structure 116 being moved (e.g., rotated around a longitudinal axis 250 based on manual manipulation of interface assembly 117) to at least partially align the fluid port 634 of the cylindrical structure 620 of the second structure 220 with the aligned fluid ports 814, 934 of the vaporizer connector assembly 818 and the vaporizer assembly 130, respectively, the reservoir 112 may be exposed to the vaporizer assembly 130 through the aligned fluid ports 634, 814, 934 such that a supply flow 904 of pre-vapor formulation held in the reservoir 112 may be introduced into the vaporizer assembly 130 from the reservoir 112 via the aligned fluid ports 634, 814, 934. As shown in FIGS. 10-10H, the vapor connector assembly 818 may include multiple fluid ports 814, the vaporizer assembly 130 may include multiple fluid ports 934, and the isolation structure 116 may include multiple fluid ports 634 that correspond with the fluid ports 934 and 814, such that the isolation structure 116 may be moved to at least partially align the multiple fluid ports 634 with separate, respective sets of aligned fluid ports 814 and 934. In particular, as shown in FIGS. 10A-10H, the vapor connector assembly 818 may include two fluid ports 814, the vaporizer assembly 130 may include two fluid ports 934, and the isolation structure 116 may include two fluid ports 634 that correspond with separate sets of aligned fluid ports 934 and 814.

As further shown in FIGS. 10A-10F, an outlet assembly 910 may be coupled with the vapor generator assembly 110 to couple conduit 914 with outlet port 144 and to isolate fluid port 114 from an exterior of at least the reservoir 112.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A vapor generator assembly comprising:
 a reservoir configured to hold a pre-vapor formulation, the reservoir including a first fluid port extending through a housing of the reservoir, the first fluid port configured to enable fluid communication between the reservoir and an exterior of the vapor generator assembly;
 a vaporizer assembly configured to vaporize the pre-vapor formulation, the vaporizer assembly including a second fluid port extending through a housing of the vaporizer assembly, the second fluid port configured to enable fluid communication between the reservoir and the vaporizer assembly; and
 an isolation structure configured to
  move in relation to both the reservoir and the vaporizer assembly to a first position where the isolation structure exposes the first fluid port and covers the second fluid port, and
  move in relation to both the reservoir and the vaporizer assembly to a second position where the isolation structure exposes the second fluid port and covers the first fluid port, wherein the isolation structure includes a first structure, the first structure including a third fluid port extending through the first structure, the third fluid port configured to at least partially align with the first fluid port for the isolation structure to expose the first fluid port, to enable fluid communication between the reservoir and the exterior of the vapor generator assembly through the at least partially aligned first and third fluid ports, based on the isolation structure moving in relation to the reservoir and the vaporizer assembly to the first position.

2. The vapor generator assembly of claim 1, wherein the isolation structure is further configured to move in relation to both the reservoir and the vaporizer assembly to a third position where the isolation structure covers the first fluid port and covers the second fluid port.

3. The vapor generator assembly of claim 1, wherein the reservoir can be refilled through the first fluid port when the isolation structure is in the first position where the isolation structure exposes the first fluid port and covers the second fluid port.

4. The vapor generator assembly of claim 1, wherein the housing of the vaporizer assembly and the housing of the reservoir form at least a portion of a common housing.

5. The vapor generator assembly of claim 1, wherein
the isolation structure includes a second structure, the second structure including a fourth fluid port extending through the second structure, the fourth fluid port configured to at least partially align with the second fluid port for the isolation structure to expose the second fluid port, based on the isolation structure moving in relation to the reservoir and the vaporizer assembly to the second position.

6. The vapor generator assembly of claim 5, wherein
the second structure includes a cylindrical structure, the fourth fluid port extending through the cylindrical structure.

7. The vapor generator assembly of claim 1, further comprising:
a vaporizer connector assembly configured to detachably couple the vaporizer assembly and the reservoir, the vaporizer connector assembly including a fourth fluid port extending through the vaporizer connector assembly, the fourth fluid port configured to align with the second fluid port, and the isolation structure exposes the second fluid port and the fourth fluid port in the second position.

8. An e-vaping device, comprising:
the vapor generator assembly of claim 1; and
a power supply assembly coupled to the vapor generator assembly, the power supply assembly including a power supply, the power supply assembly configured to supply electrical power from the power supply to the vaporizer assembly.

9. The e-vaping device of claim 8, wherein the power supply is a rechargeable battery.

10. The e-vaping device of claim 8, wherein the power supply assembly is configured to decouple from the vapor generator assembly.

11. A reservoir assembly for an e-vaping device, the reservoir assembly comprising:
a reservoir configured to hold a pre-vapor formulation, the reservoir including a first fluid port extending through a housing of the reservoir, the first fluid port configured to enable fluid communication between the reservoir and an exterior of the reservoir assembly;
a vaporizer connector assembly configured to couple with a vaporizer assembly, the vaporizer connector assembly including a second fluid port extending through the vaporizer connector assembly, the second fluid port configured to enable fluid communication between the reservoir and the exterior of the reservoir assembly through the vaporizer connector assembly; and
an isolation structure configured to
move in relation to both the reservoir and the vaporizer connector assembly to a first position where the isolation structure exposes the first fluid port and covers the second fluid port, and
move in relation to both the reservoir and the vaporizer connector assembly to a second position where the isolation structure exposes the second fluid port and covers the first fluid port,
wherein the isolation structure includes a first structure, the first structure including a third fluid port extending through the first structure, the third fluid port configured to at least partially align with the first fluid port for the isolation structure to expose the first fluid port, to enable fluid communication between the reservoir and the exterior of the reservoir assembly through the at least partially aligned first and third fluid ports.

12. The reservoir assembly of claim 11, wherein the isolation structure is further configured to move in relation to both the reservoir and the vaporizer connector assembly to a third position where the isolation structure covers the first fluid port and covers the second fluid port.

13. The reservoir assembly of claim 11, wherein
the isolation structure includes a second structure, the second structure including a fourth fluid port extending through the second structure, the fourth fluid port configured to at least partially align with the second fluid port for the isolation structure to expose the second fluid port.

14. The reservoir assembly of claim 13, wherein
the second structure includes a cylindrical structure, the fourth fluid port extending through the cylindrical structure.

15. The reservoir assembly of claim 11, wherein
the isolation structure includes a second structure, the second structure includes a cylindrical structure, the second structure includes a fourth fluid port extending through the second structure, the fourth fluid port configured to at least partially align with the second fluid port for the isolation structure to expose the second fluid port.

16. The reservoir assembly of claim 11, wherein the vaporizer connector assembly is configured to detachably couple with the vaporizer assembly.

17. A vapor generator assembly, comprising:
a reservoir configured to hold a pre-vapor formulation, the reservoir including a first fluid port configured to enable fluid communication between the reservoir and an exterior of the reservoir;
a vaporizer assembly including a second fluid port configured to enable fluid communication between the reservoir and the vaporizer assembly; and
an isolation structure configured to
move in relation to both the reservoir and the vaporizer assembly to a first position where the isolation structure enables fluid communication through the first fluid port and disables fluid communication through the second fluid port, and move in relation to both the reservoir and the vaporizer assembly to a second position where the isolation structure enables fluid communication through the second fluid port and disables fluid communication through the first fluid port,
wherein the isolation structure includes a first structure, the first structure including a third fluid port extending through the first structure, the third fluid port configured to at least partially align with the first fluid port for the isolation structure to enable fluid communication between the reservoir and the exterior of the reservoir through the at least partially aligned first and third fluid ports based on the isolation structure moving to tire first position.

18. The vapor generator assembly of claim 17, wherein the isolation structure is further configured to move in relation to both the reservoir and the vaporizer assembly to a third position where the isolation structure disables fluid communication through the second fluid port and disables fluid communication through the first fluid port.

\* \* \* \* \*